United States Patent
Musa et al.

(10) Patent No.: US 9,993,559 B2
(45) Date of Patent: *Jun. 12, 2018

(54) N-ALKYL LACTAM ETHERS, AND COMPOSITIONS AND USES THEREOF

(71) Applicant: ISP INVESTMENTS LLC, Wilmington, DE (US)

(72) Inventors: Osama M. Musa, Kinnelon, NJ (US); Kolazi S. Narayanan, Wayne, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/166,409

(22) Filed: May 27, 2016

(65) Prior Publication Data

US 2016/0271254 A1 Sep. 22, 2016

Related U.S. Application Data

(63) Continuation of application No. 14/057,075, filed on Oct. 18, 2013, now Pat. No. 9,351,484, which is a
(Continued)

(51) Int. Cl.
| | |
|---|---|
| C07D 401/12 | (2006.01) |
| A61K 47/22 | (2006.01) |
| C07D 403/12 | (2006.01) |
| B01F 17/00 | (2006.01) |
| C07D 223/10 | (2006.01) |
| C07D 207/27 | (2006.01) |
| C07D 211/76 | (2006.01) |
| C11D 7/26 | (2006.01) |
| C11D 7/32 | (2006.01) |
| C09D 7/00 | (2018.01) |
| C09D 7/12 | (2006.01) |
| C09D 9/00 | (2006.01) |
| A61K 9/00 | (2006.01) |
| A61K 47/18 | (2017.01) |
| A61K 9/70 | (2006.01) |
| A01N 25/02 | (2006.01) |
| A61K 8/49 | (2006.01) |
| A61Q 19/00 | (2006.01) |
| C08K 5/3415 | (2006.01) |
| C09D 11/36 | (2014.01) |
| C09K 3/18 | (2006.01) |
| C11D 3/43 | (2006.01) |
| A01N 43/653 | (2006.01) |
| A01N 43/78 | (2006.01) |
| A01N 53/00 | (2006.01) |
| A61K 8/58 | (2006.01) |
| A61K 31/405 | (2006.01) |
| A61K 31/4174 | (2006.01) |

(Continued)

(52) U.S. Cl.
CPC .............. *A61K 47/22* (2013.01); *A01N 25/02* (2013.01); *A01N 43/653* (2013.01); *A01N 43/78* (2013.01); *A01N 53/00* (2013.01); *A61K 8/4913* (2013.01); *A61K 8/58* (2013.01); *A61K 9/0014* (2013.01); *A61K 9/7084* (2013.01); *A61K 31/405* (2013.01); *A61K 31/4174* (2013.01); *A61K 31/65* (2013.01); *A61K 31/7048* (2013.01); *A61K 47/18* (2013.01); *A61Q 5/02* (2013.01); *A61Q 19/00* (2013.01); *B01D 53/1468* (2013.01); *B01D 53/1487* (2013.01); *B01D 53/1493* (2013.01); *B01F 17/0042* (2013.01); *C07D 207/27* (2013.01); *C07D 211/76* (2013.01); *C07D 223/10* (2013.01); *C07D 401/12* (2013.01); *C07D 403/12* (2013.01); *C08F 2/06* (2013.01); *C08K 5/3415* (2013.01); *C08L 71/02* (2013.01); *C09D 7/001* (2013.01); *C09D 7/1233* (2013.01); *C09D 9/005* (2013.01); *C09D 11/033* (2013.01); *C09D 11/36* (2013.01); *C09D 17/002* (2013.01); *C09K 3/00* (2013.01); *C09K 3/18* (2013.01); *C09K 8/524* (2013.01); *C09K 15/30* (2013.01); *C10M 133/44* (2013.01); *C11D 3/32* (2013.01); *C11D 3/43* (2013.01); *C11D 7/263* (2013.01); *C11D 7/3281* (2013.01); *G01N 21/88* (2013.01); *H01M 10/056* (2013.01); *A61Q 17/005* (2013.01); *C08L 2201/56* (2013.01); *C09K 2208/22* (2013.01); *C10M 2215/224* (2013.01)

(58) Field of Classification Search
CPC .................................................... C07D 401/12
See application file for complete search history.

(56) References Cited

PUBLICATIONS

Beck et al. (Journal of Polymer Science, Part A:Polymer Chemistry (1989), 27(2), 725-8).

(Continued)

*Primary Examiner* — Bruck Kifle
(74) *Attorney, Agent, or Firm* — Thompson Hine LLP; William J. Davis

(57) ABSTRACT

Described is a class of symmetrical and asymmetrical N-alkyl lactam ethers. One preferred ether is bis-N-ethyl pyrrolidone ether. Preferred compositions and uses of the ethers are in performance chemicals, personal care, and pharmaceutical fields, where they function a variety of roles, including as a solvent, solubilizer, freezing point depressor, diluent, extracting agent, cleaning agent, degreaser, absorbent and/or dispersion agent.

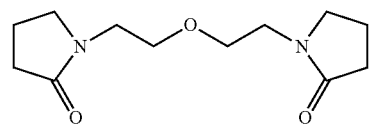

3 Claims, No Drawings

Related U.S. Application Data continuation of application No. 13/296,361, filed on Nov. 15, 2011, now abandoned.

(60) Provisional application No. 61/414,703, filed on Nov. 17, 2010.

(51) Int. Cl.
*A61K 31/65* (2006.01)
*A61K 31/7048* (2006.01)
*A61Q 5/02* (2006.01)
*B01D 53/14* (2006.01)
*C08F 2/06* (2006.01)
*C08L 71/02* (2006.01)
*C09D 11/033* (2014.01)
*C09D 17/00* (2006.01)
*C09K 3/00* (2006.01)
*C09K 8/524* (2006.01)
*C09K 15/30* (2006.01)
*C10M 133/44* (2006.01)
*C11D 3/32* (2006.01)
*G01N 21/88* (2006.01)
*H01M 10/056* (2010.01)
*A61Q 17/00* (2006.01)

(56) References Cited

PUBLICATIONS

Christjanson et al. (Proceedings of the Estonian Academy of Sciences, Chemistry (1998), 47(3), 141-154).

Sidel'kovskaya et al. (Izvestiya Akademii Nauk SSSR, Seriya Khimicheskaya (1976), (3), 605-12). Abstract.

N-ALKYL LACTAM ETHERS, AND COMPOSITIONS AND USES THEREOF

BACKGROUND OF THE INVENTION

Field of the Invention

The present invention details a class of ethers comprising at least two lactam rings, which may be the same or different. The ethers may be symmetrical or asymmetrical depending on the reactants, reaction, and/or reaction conditions. One preferred ether is bis-N-ethyl pyrrolidone ether. This and other ethers find useful service in the personal care, performance chemicals, and pharmaceutical arts, where they may serve as solvents, solubility aides, freezing point depressors, dispersing agents, reaction fluids, and cleaning agents.

Description of Related Art

There exists a great commercial need for fluids with advanced, multi-functional properties for application in performance chemicals, personal care, and pharmaceutical compositions and uses. Such fluids find utility as solvents, solubilizers, cleaning agents, extraction fluids, absorbing agent, heat transfer fluids, and dispersing fluids, among many other uses. Known fluids in these application areas often exhibit undesirable characteristics. For example, chlorinated hydrocarbons display excellent grease-cutting ability, but many have harmful toxicological profiles which limits or excludes there use, for example, in personal care compositions. In other cases an effective cleaning fluid is not water soluble, which may rule out its use in water-based applications, e.g., for household or industrial hard surface cleaning, or laundry. It may be the case that to meet toxicological, environmental, and other considerations that such fluids end up having suboptimal properties, like limited ranges in freezing/boiling point or solvency, or solubility profiles.

The current invention discloses lactam compounds and describes their compositions and uses. One preferred compound is bis-N-ethyl pyrrolidone ether.

An early disclosure of bis-N-ethyl pyrrolidone ether is provided in an article by Reppe and Mitarbeiter (1955), which teaches its sodium-catalyzed synthesis from pyrrolidone and dichlorodiethyl ether. A 50 mole percent yield of bis-N-ethyl pyrrolidone ether was reported.

Shostakovskii, et al. (1961) esterified N-hydroxyethyl pyrrolidone with the chlorides of acetic, propionic, butyric, valerianic, and caproic acids. Upon distillation of the esters they identified bis-N-ethyl pyrrolidone ether, bis-N-ethyl piperidone ether, and bis-N-ethyl caprolactam ether.

A related compound is N-ethyl-2-pyrrolidone, which is discussed in WO 2005/0900447 as a solvent, diluent, extraction agent, cleaning agent, degreasing agent, absorption agent, and/or dispersion agent, especially as a replacement for N-methyl pyrrolidone.

Also related is N-methyl pyrrolidone, also referred to as NMP and offered into commercial sale by International Specialty Products as M-Pyrol®. NMP publications include the following 18 publications by the BASF Corporation, each of which is incorporated in its entirety be reference:

The brochure "Formulating paint strippers with N-methylpyrrolidone," BASF Corporation, Chemical Intermediates, 1990, USA, Walsh, W. C., "Removal of rosin- and resin-based solder flux from electronic assemblies with N-methylpyrrolidone/water mixtures,"

Walsh, W. C., "Degreasing and solvent regeneration in metal parts, cleaning using N-methylpyrrolidone," e.g.: http://es.epa.gov/p2pubs/oaic/301.html, Walsh, W. C., "Surface Tension Modification of NMP based Paint Strippers,"

Walsh, W. C., "N-methyl pyrrolidone (NMP technical tips), removal of paints and coatings from NMP-soluble plastics,"

Walsh, W. C. (1991), "Surface tension modification of NMP-based paint strippers," in *Reducing Risk in Paint Stripping*, Washington D.C., 12-13 Feb. 1991, pp. 177-184, Economics and Technology Division; Office of Toxic Substances; United States Environmental Protection Agency, Washington D.C., 1991, Walsh, W. C., "N-methyl pyrrolidone (NMP Technical Tips), Maintenance Cleaning of Aircraft Ball Bearing Assemblies,"

Walsh, W. C., "N-methyl pyrrolidone (NMP Technical Tips); Cleaning of a Chlorinated Paraffin/Metal Stearate Based Drawing Compound Off of 1000 Ft. Long Coils of 0.25 inch, 316 Stainless Steel Tubing,"

Walsh, W. C., "N-methyl pyrrolidone (NMP Technical Tips), Chemical Warfare Resistant Coatings (CARC), Removal From Metal Surfaces,"

Walsh, W. C., W. Monahan and M. Waidrop, "Reflux Cleaning of Large Reactors with N-methyl pyrrolidone (NMP),"

Walsh, W. C., "Replacement of MEK with N-methyl pyrrolidone (NMP) in coatings plant resin clean-up operation,"

Walsh, W. C., "N-methyl pyrrolidone (NMP) technical tips, removal of polyurethane/polyurea residue from the interior surfaces of a batch reactor vessel,"

Walsh, W. C., "N-methyl pyrrolidone-cleaning applications in the urethane manufacturing and processing industries,"

M. W. Waldrop and Walsh, W. C., "Modification of a vapor degreasing machine for immersion cleaning using N-methyl pyrrolidone,"

Walsh, W. C., "Removal of N-methyl pyrrolidone from metal parts using a centrifugal dryer,"

Walsh, W. C., et al., "A process to vacuum vapor degrease metal parts with N-methyl pyrrolidone," http://es.epa.gov/techpubs/3/15413.html, Walsh, W. C., et al., "Removal of N-methyl pyrrolidone (NMP) from industrial plant exhaust air with a packed column scrubber,"

Walsh, W. C., et al., "A process to vacuum vapor degrease metal parts with N-methyl-pyrrolidone," 1997, CA Abstract No. 127:7688, Walsh, W. C., "N-methyl pyrrolidone (NMP technical tips), reclaiming or recycling of NMP," and "Electrical insulation—from wire enamel to enameled wire," 1 Beck Information, July 1992, (Beck Electrical Insulation Systems, Hamburg).

Yet another related compound is N-methyl-2-caprolactam, described in the publication K. Wehner et al., *Chem. Techn*. (8), 1977, pages 445-448, which concerns the use of N-methyl-ε-caprolactam as a selective solvent for gas neutralization, i.e. for the removal of acidic gases, such as $CO_2$ or sulfur-containing acidic gases (e.g., $H_2S$, $CH_3SH$, $C_2H_5SH$), from natural gas or synthesis gas.

U.S. Pat. No. 5,326,880, assigned to ISP Investments, teaches asymmetrical polyvinylpyrrolidonyl compounds and their uses as complexing and dispersing agents. Included as Example 4 are two asymmetrical molecules, 1-methyl-3,6-dioxa-1,8-dipyrrolidonyl octane, which has two ether linkages, and N-ethylpyrrolidonyl-pyrrolidonyl polyoxypropylene, which has two or three ether linkages.

U.S. Pat. No. 5,994,562 discloses a process for preparing N-alkenylcarboxamides by dehydration of N-(2-hydroxyalkyl)carboxamides and/or diethers. Dehydration of HEP with undoped catalysts yielded bis-N-ethyl pyrrolidone ether as an unwanted side product at concentrations up to 71%. The '562 patent is directed toward the use of desirable catalysts that reduce the bis-N-ethyl pyrrolidone ether side product to 1% or less.

Despite the development in lactam compounds, there still exists a commercial and industrial need for materials that exhibit excellent solvency and solvent compatibility/miscibility that also provide an improved safety profile. These are the objectives of the present invention, and to describe these lactam compounds, their compositions and uses thereof, especially in various performance chemicals, personal care, and pharmaceutical applications.

SUMMARY OF THE INVENTION

A broad class of ethers have been discovered, along with their compositions and uses. The ethers can be synthesized from different reactions involving one or more lactam molecules to yield symmetrical or asymmetrical ethers. These ethers find multiple applications, such as a solvent, solubilizer, diluent, extracting agent, cleaning agent, degreaser, absorbent and/or dispersion agent.

Preferred compositions and uses of the ethers are in performance chemicals, personal care, and pharmaceutical fields, where they function a variety of roles, including as solvents, solubilizers, cleaning agents, and freezing point depressors, to name but a few.

DETAILED DESCRIPTION OF PREFERRED EMBODIMENTS OF THE INVENTION

Described herein is a class of highly desirable compounds and their uses in personal care, performance chemicals, and pharmaceutical applications. Due to the flexibility in compound structure, as will be addressed later, they find function as solubilizers, stabilizers, solvents, plasticizers, freezing-point depression agents, cleaning agents, degreasers, and a host of other uses. Before describing the compounds, their compositions, and uses, it is beneficial to define a number of terms.

As used herein, the following terms have the meanings set out below:

The term halogen refers to chloro, bromo, iodo and fluoro, and is preferably bromo or chloro. The term halogenated refers to compounds having one or more halogen substituents.

The term heteroatom refers to atoms such as oxygen, nitrogen, sulfur, and phosphorus.

The term monomer refers to a repeating structural unit of a polymer. A monomer is a low molecular weight compound that can form covalent chemical bonds with itself and/or with other monomers, resulting in a polymer.

The term polymer refers to a compound comprising repeating structural units (monomers) connected by covalent chemical bonds. The definition includes oligomers. Polymers may be further derivatized (example by hydrolysis), crosslinked, grafted or end-capped. Non-limiting examples of polymers include copolymers, terpolymers, quaternary polymers, and homologues. A polymer may be a random, block, or an alternating polymer, or a polymer with a mixed random, block, and/or alternating structure. Polymers may further be associated with solvent adducts.

The term solvent adduct refers to a solvent molecule that is bonded to a compound such as a polymer by one or more covalent bonds, ionic bonds, hydrogen bonds, coordinate covalent bonds, and/or Van der Waals forces of attraction.

The term copolymer refers to a polymer consisting essentially of two types of repeating structural units (monomers). The definition includes copolymers having solvent adducts.

The term terpolymer refers to a polymer consisting essentially of three types of repeating structural units (monomers). The definition includes terpolymers having solvent adducts.

The terms ultraviolet and UV mean electromagnetic radiation, especially solar electromagnetic radiation, with a wavelength from about 100 nm to about 400 nm, and includes the UV-A, UV-B, and UV-C subclassifications of such radiation.

The term UV-A means ultraviolet electromagnetic radiation with a wavelength from about 320 nm to about 400 nm, and includes UV-A1 (from about 340 nm to about 400 nm) and UV-A2 (from about 320 nm to about 340 nm).

The term UV-B means ultraviolet electromagnetic radiation with a wavelength from about 290 nm to about 320 nm.

The term UV-C means ultraviolet electromagnetic radiation with a wavelength from about 200 nm to about 290 nm.

The term UV absorber means any entity that absorbs, scatters, and/or reflects UV radiation.

The term personal care composition refers to such illustrative non-limiting compositions as skin, sun, oil, hair, cosmetic, and preservative compositions, including those to alter the color and appearance of the skin. Potential personal care compositions include, but are not limited to, polymers for increased flexibility in styling, durable styling, increased humidity resistance for hair, skin, and color cosmetics, sun care water-proof/resistance, wear-resistance, and thermal protecting/enhancing compositions.

The term performance chemicals composition refers to any non-personal care composition. Performance chemicals compositions serve a broad spectrum of arts, and include non-limiting compositions such as: adhesives; agricultural, biocides, coatings, electronics, household-industrial-institutional (HI&I), inks, membranes, metal fluids, oilfield, paper, paints, plastics, printing, plasters, and wood-care compositions.

The term pharmaceutical composition refers to any composition finding utility on or in man or animal that comprises one or more active ingredients. This definition includes those compositions sold with and without prescription, branded and unbranded products, as well as those compositions sold into homeopathy markets.

All percentages, ratio, and proportions used herein are based on a weight basis unless otherwise specified.

Description of the Ethers

A class of ethers has been discovered that resolve problems noted in the prior art. The ethers are the family of N-alkyl lactam ethers are represented by the structure:

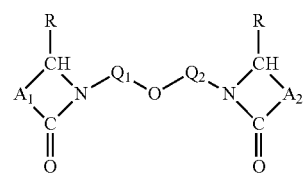

(1)

wherein:
A₁ and A₂ are independently selected alkyl groups having 2 to 50 carbon atoms, wherein 2 to 4 carbon atoms reside in the lactam ring between the

group and the

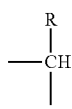

group;
Q₁ and Q₂ are independently selected from the group consisting of functionalized and unfunctionalized alkyl and cycloalkyl groups and combinations thereof, wherein any of the beforementioned groups may be with or without heteroatoms; and
each R is independently selected from the group consisting of hydrogen, and functionalized and unfunctionalized alkyl and cycloalkyl groups, and combinations thereof, wherein any of the beforementioned groups may be with or without heteroatoms;
with the provision that A₁, A₂, Q₁, and Q₂ are not all ethyl and both R are not hydrogen.

The family of ethers represented by structure (1) can be subdivided into two categories: symmetrical and asymmetrical ethers. Symmetrical ethers are those ethers wherein the lactam ring groups A₁ and A₂ are the same, and the spacer groups Q₁ and Q₂ are the same, and all corresponding R groups the same. By way of illustration and without restriction, examples of symmetrical ethers having pyrrolidone-, piperidone-, and caprolactam-based chemistries include:

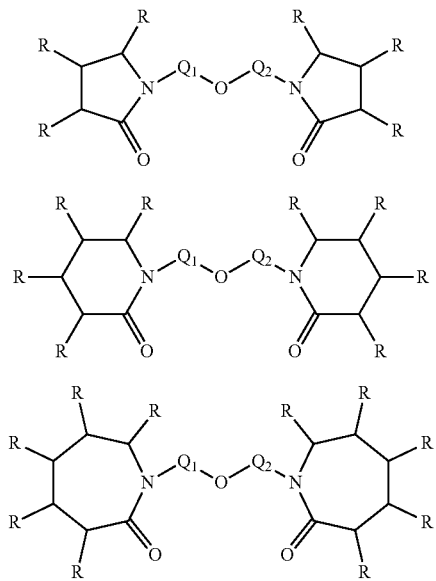

wherein the spacer groups Q₁ and Q₂ are selected from the group consisting of functionalized and unfunctionalized alkyl and cycloalkyl groups, wherein any of the beforementioned groups may be with or without heteroatoms; and each R is independently selected from the group consisting of hydrogen, and functionalized and unfunctionalized alkyl and cycloalkyl groups, wherein any of the beforementioned groups may be with or without heteroatoms; with the exception that in structure (2) the spacer groups Q₁ and Q₂ are not ethyl and each R is not hydrogen.

Specific examples of symmetrical ethers of the invention include compounds having the following structures:

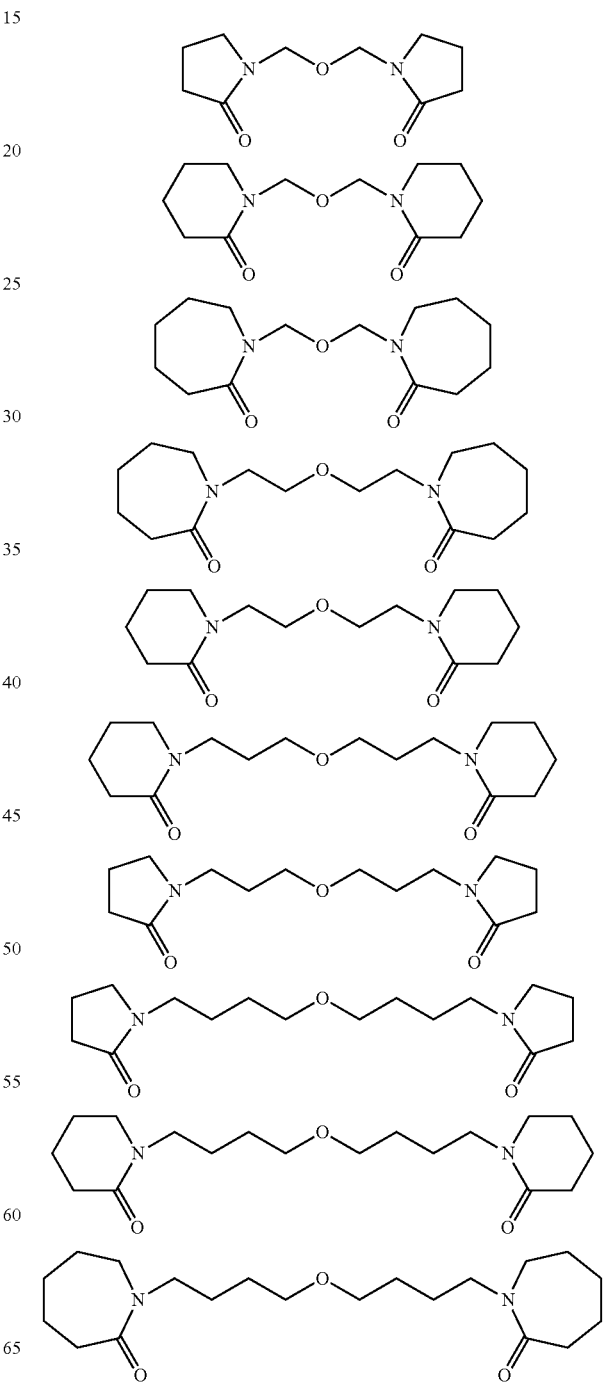

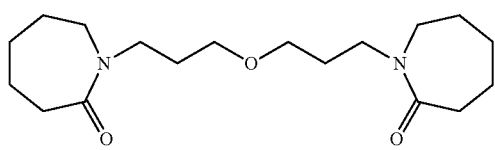

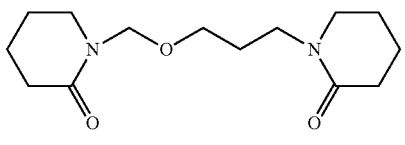

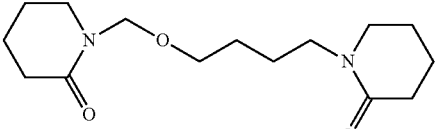

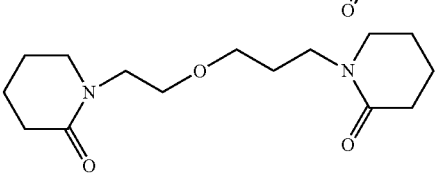

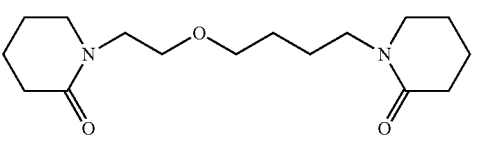

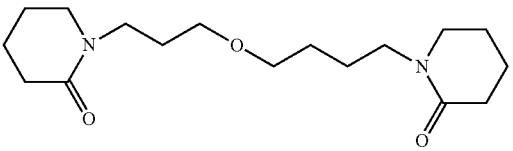

One skilled in the art will recognize that structure (1) also describes asymmetrical ethers, which are ethers wherein at least one of $A_1$ and $A_2$ are not the same, and/or $Q_1$ and $Q_2$ are not the same, and/or at least one pair of corresponding R groups are not the same Given the multiplicity of these combinations, the invention embraces many more asymmetrical ethers than their symmetrical counterparts. Several possibilities exist: asymmetrical-non-mixed ethers, ($A_1$ and $A_2$ are the same, but $Q_1$ and $Q_2$ are not the same and/or corresponding pairs of R groups differ), and asymmetrical-mixed ethers ($A_1$ and $A_2$ are not the same, $Q_1$ and $Q_2$ are or are not the same, and/or corresponding pairs of R groups are or are not the same).

One preferred sub-class of asymmetrical-non-mixed ethers of the invention are those having the same lactam ring, but different spacer groups. Examples of these asymmetrical-non-mixed ethers include:

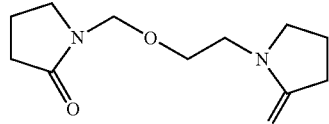

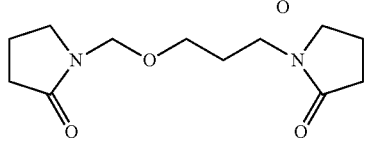

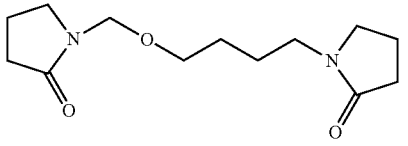

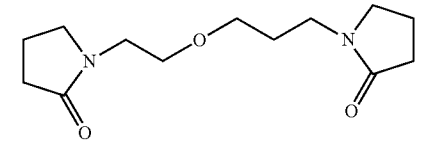

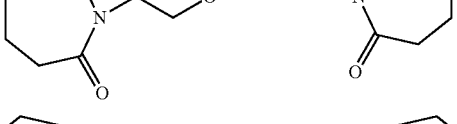

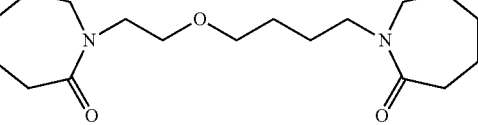

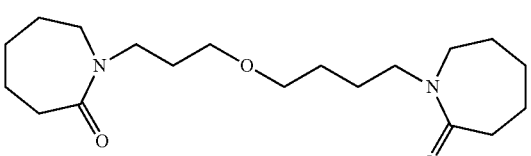

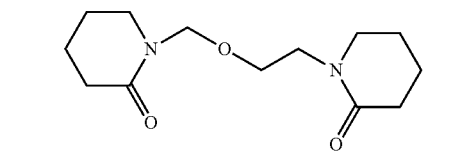

-continued

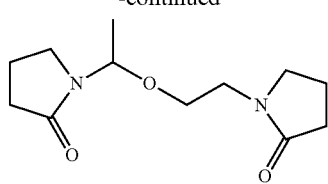

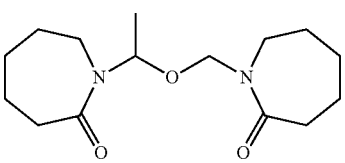

A second preferred sub-class of asymmetrical-non-mixed ethers are those ethers having structures represented by:

(5)

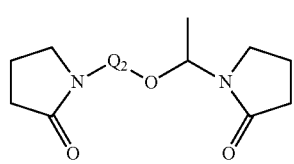

(6)

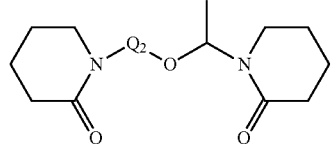

(7)

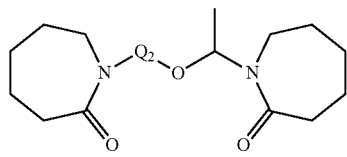

wherein $Q_2$ retains its earlier definition. Examples of these asymmetrical-non-mixed ethers include:

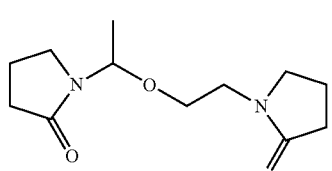

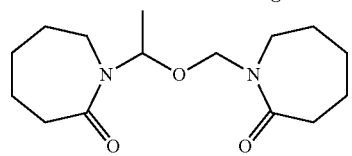

In addition to the described ethers, the invention also provides for asymmetrical-mixed ethers, which occur when $A_1$ and $A_2$ are not the same. Specific examples of pyrrolidone-, piperidone-, and caprolactam-based asymmetrical-mixed ethers include those having the structures:

(8)

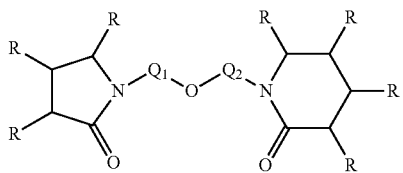

(9)

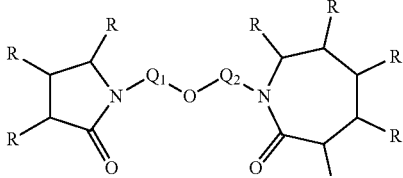

(10)

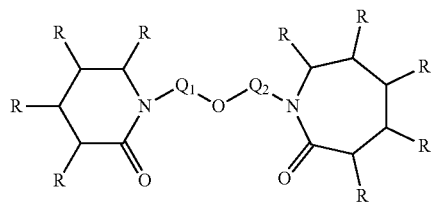

wherein $Q_1$, $Q_2$, and R have the same meaning as described earlier.

Other asymmetrical-mixed ethers are those represented by the structures:

(11)

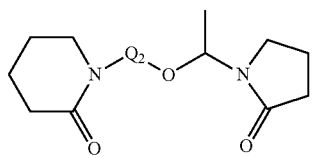

(12)

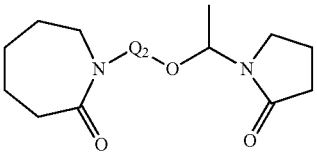

(13)

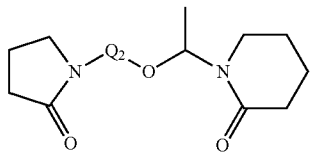

(14)

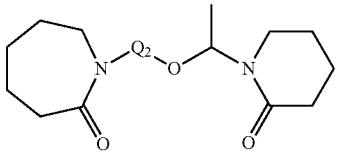

(15)

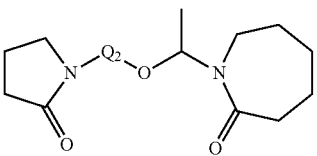

-continued
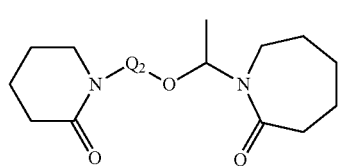
(16)
wherein Q₂ has the same meaning as described earlier.
Specific examples of asymmetrical-mixed ethers of the invention include ethers represented by the following structures:
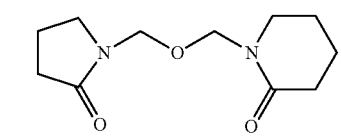
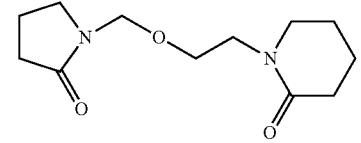
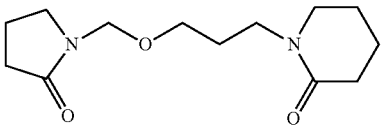
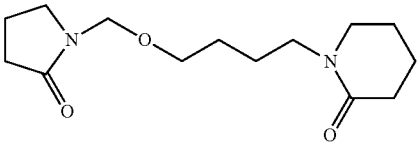
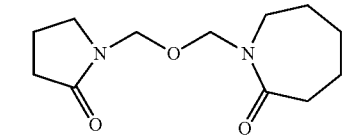
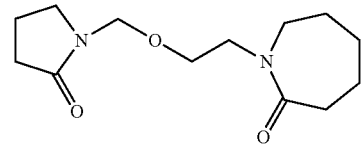
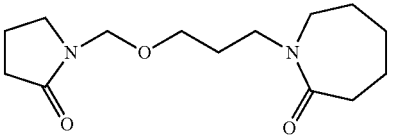
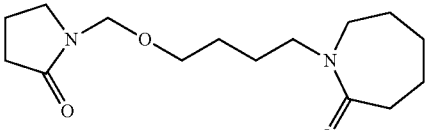
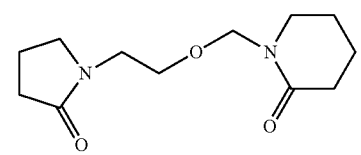
-continued
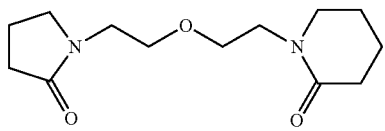
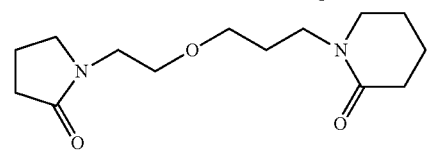
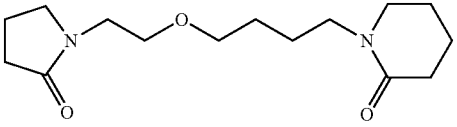
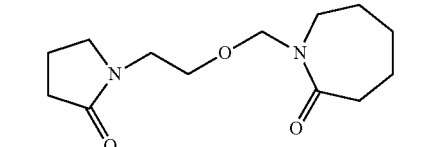
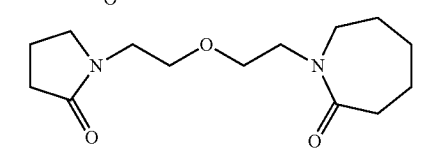
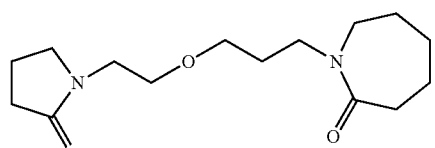
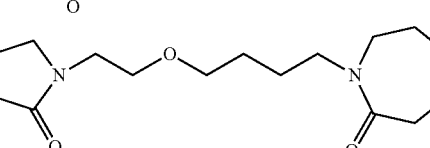
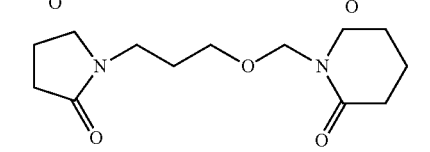
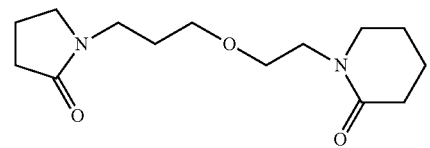
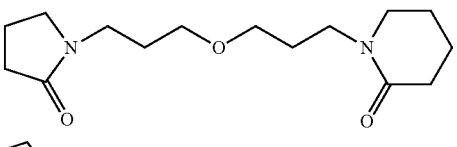
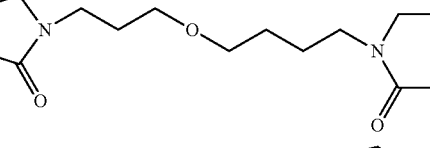
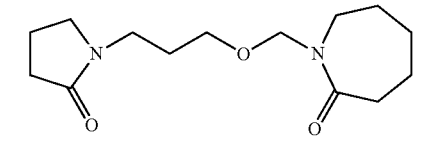

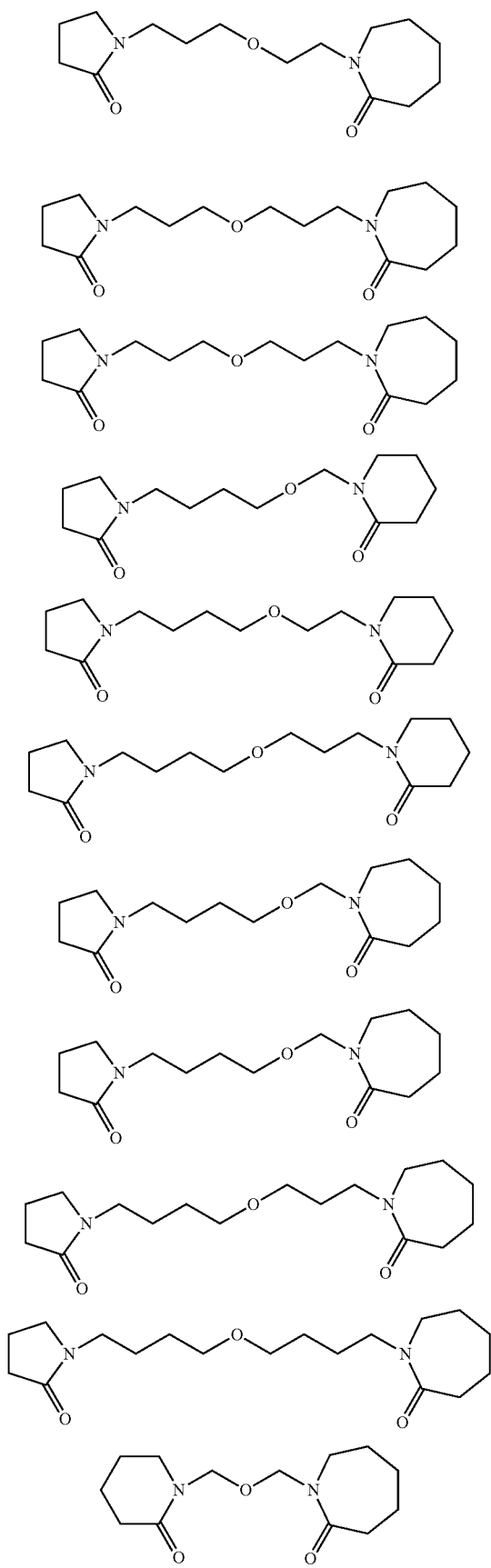

-continued

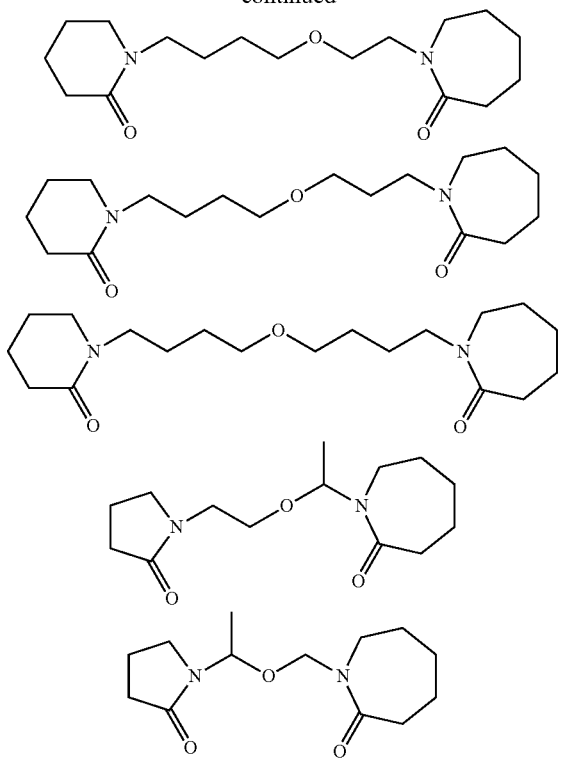

Clearly, other ethers of the invention are contemplated than the specific structures shown above, including ethers wherein $Q_1$, $Q_2$, or both $Q_1$ and $Q_2$ comprise more than four carbon atoms, and those ethers having one or more non-hydrogen R groups (e.g., lower alkyl groups having four or fewer carbon atoms like methyl, ethyl, propyl, or halogen).

Description of the Synthesis Method

The inventive ethers can be synthesized from a number of routes, such as the dehydration of alcohols, and Williamson ether synthesis. The former may be preferred for the production of symmetrical ethers, but it is understood that the asymmetrical ethers also can be produced by alcohol dehydration and the resulting mixture of ethers can be purified by methods like chromatography, distillation, and/or precipitation. The Williamson method, however, can be used to prepare both symmetrical and asymmetrical ethers. A description of these methods is provided in *Organic Chemistry, sixth edition* by R. T. Morrison and R. N. Boyd, which is incorporated in its entirety by reference.

Examples of ethers and synthesis methods for ethers of the present invention include:
  the synthesis of N-hydroxymethyl-2-pyrrolidone from 2-pyrrolidone, potassium hydroxide and p-formaldehyde, as described in U.S. Pat. No. 4,105,671, which is incorporated herein its entirety by reference;
  the synthesis of N-hydroxypropyl-2-pyrrolidone, disclosed by Reppe et al. in *Justus Liebigs Annalen der Chemie*, 1955, vol. 596, p. 1202;
  the synthesis of N-hydroxyethyl-2-piperidone, by a method described by Gracias et al., in *Tetrahedron*, 1997, vol. 53, no. 48, p. 16241, which is incorporated herein its entirety by reference;
  the synthesis of N-hydroxypropyl-2-piperidone taught by Gracias et al., ibid.;
  the synthesis of N-hydroxymethyl-2-caprolactam as disclosed in U.S. Pat. No. 4,769,454, which is incorporated herein its entirety by reference;
  the synthesis of N-hydroxyethyl-2-caprolactam, taught by Gracias et al., ibid.; and
  the synthesis of N-hydroxypropyl-2-caprolactam, using a method by Gracias et al., in *J. Org. Chem.*, 1996, vol. 61, no. 1, p. 10.

Commercial sources and other syntheses methods for these and other N-hydroxyalkyl lactam reactants can be identified using various Internet-based sites, like https://www.reaxys.com, https://www.emolecules.com, and http://pubchem.ncbi.nlm.nih.gov/.

A preferred synthesis route is the dehydration of alcohols, which generically includes the steps: (a) reacting a first N-hydroxyalkyl lactam and a second N-hydroxyalkyl lactam (being the same or different from the first) with an acid catalyst; (b) heating the reaction system, and, optionally (c) removing water from the reaction system.

To the first and second N-hydroxyalkyl lactams is added an acid catalyst. Examples of suitable acids include, without limitation: the hydrogen halides and their solutions (such as sulfuric acid, nitric acid, and phosphoric acid), and sulfonic acids (such as methanesulfonic acid, ethanesulfonic acid, benzenesulfonic acid, toluenesulfonic acid, and trifluoromethanesulfonic acid). High yields and purities can be attained given the proper experimental conditions of temperature, time, catalyst, and reactant and catalyst amounts.

In one embodiment of the synthesis method, the first and second N-hydroxyalkyl lactams mentioned above are the same, and the resulting ether is a symmetrical bis-N-alkyl lactam ether, as described earlier. By way of example, the synthesis of one preferred ether, bis-N-ethyl pyrrolidone ether, is provided by the dehydration of N-hydroxyethyl-2-pyrrolidone using an acid catalyst:

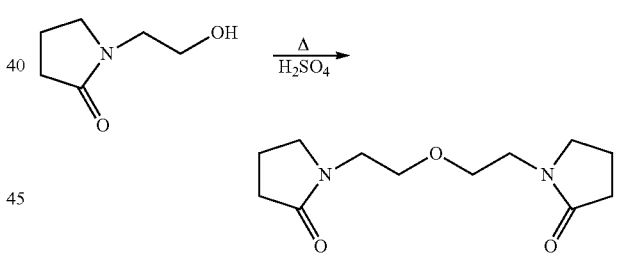

Other ethers that can be produced include another preferred ether of the invention, bis-N-methyl caprolactam ether:

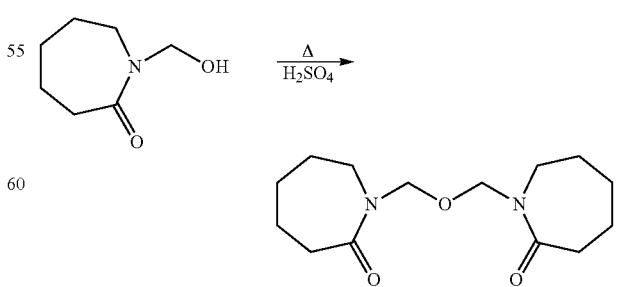

Contemplated is the synthesis wherein the first and second N-hydroxyalkyl lactams are different, so that the synthesized ether is one of the asymmetrical ethers. When two or more different N-hydroxyalkyl lactams are used in the synthesis, then the product may constitute of mixture of symmetrical and asymmetrical ethers, which may be purified using known methods, such as distillation, chromatography, or precipitation techniques.

In addition to those methods, also provided is the synthesis of ethers as an anti-Markovnikov reaction product between an N-vinyl lactam and an N-hydroxyalkyl lactam:

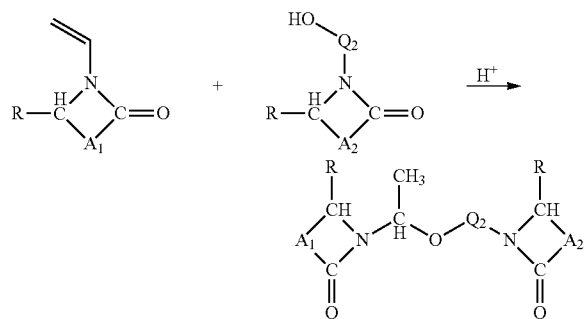

wherein:
A₁ and A₂ are independently selected alkyl groups having 2 to 50 carbon atoms, wherein 2 to 4 carbon atoms reside in the lactam ring between the

group and the

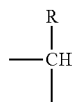

group;
$Q_1$ and $Q_2$ are independently selected from the group consisting of functionalized and unfunctionalized alkyl and cycloalkyl groups and combinations thereof, wherein any of the beforementioned groups may be with or without heteroatoms; and
each R is independently selected from the group consisting of hydrogen, and functionalized and unfunctionalized alkyl and cycloalkyl groups, and combinations thereof, wherein any of the beforementioned groups may be with or without heteroatoms.

The ethers produced by this method may have the same or different lactam rings. For example, ethers represented by structures (5)-(7) and (11)-(16) can be produced by this method by reacting the appropriate N-vinyl lactam and N-hydroxyalkyl lactam reagents.

Compositions Comprising the Ethers

Except when the application allows and/or requires the neat (pure or essentially pure) form of one or more ethers, i.e., for use as a cleaning agent or solvent, then compositions will be formulated having the designated ether(s) and one or more additional ingredients. Given the versatility in the compounds represented by formula (1) and purities that can be attained, a wide-ranging variety of compositions can be devised to serve the personal care, performance chemicals, and pharmaceutical arts. Each of these art areas will be described briefly to illustrate the many kinds of compositions where the ethers find use.

First, though, it is important to understand that often the same types of ingredients are used across these areas, such that any specific selection may be based on factors like molecular weight, purity, and impurity profile. Co-ingredients fitting this description include: solvents, polymers, liquid carriers, active ingredients, surfactants, wetting agents, emulsifiers, rheology modifiers/thickeners, lubricants, diluents, humectants, anti-oxidants, preservatives, cleaning agents, dyes, inks, solvents, freezing point depressors, salts, thickeners, peroxides, and oils. Of course, combinations of these ingredients may be used.

Water is one important cosolvent embraced by the invention for all compositions thereof. Due to electron delocalization within the lactam ring, inventive ethers of lower molecular weight are miscible with water. For example, the symmetrical ether bis-N-ethyl pyrrolidone ether is water soluble in all proportions. Ethers having from 1 to 4 carbon atoms in the spacer groups $Q_1$ and $Q_2$ (such as methyl, ethyl, and propyl) may especially exhibit water solubility, which can be verified by one skilled in the art. Water solubility decreases as the molecular weight of the lactam ring increases, so that smaller spacer groups $Q_1$ and/or $Q_2$ may be needed to retain water solubility. Alternatively, the spacer groups and/or the lactam ring can be functionalized with hydrophilic groups like hydroxyl groups to improve water solubility. As illustrated in the Examples, blends of bis-N-ethyl pyrrolidone ether and water exhibit surprisingly low freezing points that are even lower than ethylene glycol/water blends.

Performance Chemicals Compositions

The ethers of the invention may be formulated into performance chemicals compositions, meaning those compositions that are not intended for use on or in the body of a human or animal. As exemplified in the Examples, a wide variety of performance chemicals can contain the N-hydroxyalkyl lactams, especially bis-N-ethyl pyrrolidone, such as acaricides, batteries, cleaning, coating, encapsulation, fragrance, imaging, ink, oilfield, laundry pre-wash/stain remover, bird repellant, insect repellent, insecticide, termite-control, herbicide, slimacide, fungicide, membrane, molded part, polishing, adhesive, hose/tubing, packaging, printing, and wood-care compositions. Included in this performance chemicals category are compositions for the manufacture and/or processing of pharmaceuticals, especially pharmaceutical active ingredients. (Pharmaceutical compositions per se are considered later separately.)

In these performance chemicals compositions the ethers may exist with one or more cosolvents or solvents, particularly when the ether(s) partially or completely replace solvents having an undesirable safety profile, such as chlorinated solvents (e.g., methylene chloride, trichloroethane), aliphatic solvents (e.g., ketones and other ethers), and aromatic solvents (e.g., benzene, toluene). The use of these and similar solvents may be limited to performance chemicals applications due to their safety profiles. Yet, In these instances replacement of the less desirable solvent with the ethers described here may result in lower toxicity, lower emissions, and/or improved degradability (including biodegradability).

Often these compositions also comprise one or more active ingredients, such as one or more biocides, insecticides, fungicides, herbicides, slimacides, mildewicides, acaricides, insect repellents, or UV absorbers (especially for plastic or wood care).

However, active ingredients are not a requirement in these compositions, because compositions having the ethers also find usefulness as paint/graffiti removers, solvents, and reaction media. Alternatively, the compositions may also contain one more polymers. This description is not to say, though, that active ingredients cannot be included in compositions having active ingredients, since polymers may help alter the composition's rheology, e.g., providing semisolid, paste-like, or gel consistencies, especially when such rheology is advantageous to the composition's final delivery and/or use.

Personal Care Compositions

The ethers also can be used in personal care compositions that include skin lotion, skin cremes, skin ointments, skin salves, anti-aging crèmes, moisturizers, deodorants, tanning agents, sun blocks, foundations, concealers, eyebrow pencils, eye shadows, eye liners, mascaras, rouges, finishing powders, lipsticks, lip gloss, nail polish, make-up removers, nail polish removers, shampoos, rinse-off conditioners, leave-on conditioners, hair styling gels, hair mousses, hair sprays, styling aides, hair colors, and hair color removers. These compositions can benefit from the dissolving, dispersing, freezing-point depression, viscosity, and mildness, especially of bis-N-ethyl pyrrolidone ether.

As mentioned for performance chemicals compositions, the ethers can be formulated in personal care compositions with one or more cosolvents or solvents. Again, the ethers may replace some or all of such solvents (which also may be known as cosmetic solvents) such as diisopropyl adipate, phenyl ethyl benzoate, glycerin, diisopropyl sebacate, diethylhexyl adipate, diethylhexyl succinate, butylene glycol, cyclopentasiloxane, caprylic/capric triglycerides, paraffinum liquidum, cyclomethicone, benzyl alcohol, limonene, isohexadecane, pentylene glycol, isopropyl palmitate, isopropyl myristate, octyldodecanol, isododecane, PEG-4, PEG-8, PEG-12, PEG-20, PEG-75, PEG-90, PEG-150, hexalyene glycol, glycol, cyclotetrasiloxane, lanolin oil, lanolin oil, acetone, ethanol, 1- and 2-propanol, silicone oils, vegetable oils, and hydrocarbons, including derivatized variants thereof. For example, these solvents may aide in solubilizing, dispersing, carrying, and/or distributing agents (including active ingredients) typical for formulations used on the skin, hair, eye lids, lips, or nails. Consider nail polish remover, for which acetone-containing products may be made more friendly in with ethers of the invention.

One type of preferred personal care composition is the class of materials known for protecting the user from ultraviolet (UV) damage, for example, of the skin and/or hair. Some of the marketed terms these materials are sold by include suncare, all-day care, sun block, and skin care with UV absorbers. Suncare composition frequently contain one or more UV absorbers, like the following active ingredients: octyl salicylate (2-ethylhexyl salicylate, Escalol® 587); pentyl dimethyl PABA; octyl dimethyl PABA (padimate O, Escalol® 507); benzophenone-1; benzophenone-6 (Uvinul® D-49); 2-(2H-benzotriazole-2-yl)-4,6-di-tert-pentylphenol (Uvinul® 3028); ethyl-2-cyano-3,3-diphenylacrylate (Uvinul® 3035); homomenthyl salicylate (homosalate); bis-ethylhexyloxyphenol methoxyphenyl triazine (bemotrizinol, Tinosorb® S); methyl-(1,2,2,6,6-pentamethyl-4-piperidyl)-sebacate (Uvinul® 4092H); benzenepropanoic acid, 3,5-bis (1,1-dimethyl-ethyl)-4-hydroxy-, C7-C9 branched alkyl esters (Irganox® 1135); 2-(2H-benzotriazole-2-yl)-4-methylphenol (Uvinul® 3033P); diethylhexyl butamido triazone (iscotrizinol); amyl dimethyl PABA (lisadimate, glyceryl PABA); 4,6-bis(octylthiomethyl)-o-cresol (Irganox® 1520); CAS number 65447-77-0 (Uvinul® 5062H, Uvinul® 5062GR); red petroleum; ethylhexyl triazone (Uvinul® T-150); octocrylene (Escalol® 597); isoamyl-p-methoxycinnamate (amiloxate, Neo Heliopan® E1000); drometrizole; titanium dioxide; 2,4-di-tert-butyl-6-(5-chloro-2H-benzotriazole-2-yl)-phenol (Uvinul® 3027); 2-hydroxy-4-octyloxybenzophenone (Uvinul® 3008); benzophenone-2 (Uvinul® D-50); diisopropyl methylcinnamate; PEG-25 PABA; 2-(1, 1-dimethylethyl)-6-[[3-(1,1-demethylethyl)-2-hydroxy-5-methylphenyl]methyl-4-methylphenyl acrylate (Irganox® 3052); drometrizole trisiloxane (Mexoryl® XL); menthyl anthranilate (meradimate); bis-(1,2,2,6,6-pentamethyl-4-piperidyl)-sebacate; butyl methoxydibenzoylmethane (avobenzone, Escalol® 517); 2-ethoxyethyl p-methoxycinnamate (cinnoxate); benzylidene camphor sulfonic acid (Mexoryl® SL); dimethoxyphenyl-[1-(3,4)]-4,4-dimethyl 1,3-pentanedione; zinc oxide; N, N'-hexane-1,6-diylbis[3-(3,5-di-tert-butyl-4-hydroxyphenylpropionamide)] (Irganox® 1098); pentaerythritol tetrakis[3-(3,5-di-tert-butyl-4-hydroxyphenyl)propionate] (Irganox® 1010); 2,6-di-tert-butyl-4-[4,6-bis(octylthio)-1,3,5-triazin-2-ylamino]phenol (Irganox® 565); 2-(2H-benzotriazole-2-yl)-4,6-bis(1-methyl-1-phenylethyl)phenol (Uvinul® 3034); trolamine salicylate (triethanolamine salicylate); diethylanolamine p-methoxycinnamate (DEA methoxycinnamate); polysilicone-15 (Parsol® SLX); CAS number 152261-33-1 (Uvinul® 5050H); 4-methylbenzylidene camphor (Eusolex® 6300, Parsol® 5000); bisoctrizole (Tinosorb® M); benzenamine, N-phenyl-, reaction products with 2,4,4-trimethylpentene (Irganox® 50507); sulisobenzone, Escalol®577); (2-ethylhexyl)-2-cyano-3,3-diphenylacrylate (Uvinul® 3039); digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-; bis-(2,2,6,6-tetramethyl-4-piperidyl)-sebacate (Uvinul® 4077H); benzophenone-5; 1,3,5-tris(3,5-di-tert-butyl-4-hydroxybenzyl)-1,3,5-triazine-2,4,6(1H,3H, 5H)-trione (Irganox® 3114); hexamethylendiamine (Uvinul® 4050H); benzophenone-8 (dioxybenzone); ethyl-4-bis(hydroxypropyl) aminobenzoate (roxadimate); 6-tert-butyl-2-(5-chloro-2H-benzotriazole-2-yl)-4-methylphenol (Uvinul® 3026); p-aminobenzoic acid (PABA); 3,3',3",5,5', 5"-hexa-tert-butyl-α-α'-α"-(mesitylene-2,4,6-triyl)tri-p-cresol (Irganox® 1130); lawsone with dihydroxyacetone; benzophenone-9 (Uvinul® DS-49); benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor (Mexoryl® SD); terephthalylidene dicamphor sulfonic acid; camphor benzalkonium methosulfate (Mexoryl® SO); bisdisulizole disodium (Neo Heliopan® AP); etocrylene; ferulic acid; 2-(2H-benzotriazole-2-yl)-4-(1,1,3,3-tetramethylbutyl)-phenol (Uvinul® 3029); 4,6-bis(dodecylthiomethyl)-o-cresol (Irganox® 1726); beta-2-glucopyranoxy propyl hydroxy benzophenone; phenylbenzimidazole sulfonic acid (ensulizole, Eusolex® 232, Parsol® HS); benzophenone-3 (oxybenzone, Escalol® 567); diethylamine hydroxybenzoyl hexylbenzoate (Uvinul® A Plus); 3',3'-diphenylacryloyl)oxy]methyl}-propane (Uvinul® 3030); and ethylhexyl p-methoxycinnamate (Escalol® 557). It is recognized that the availability of UV absorbers in personal care compositions often depends on local regulatory laws; hence, the above list may include UV absorbers that are not allowed in certain regions.

Preferred are those personal care composition having one or more ethers of the invention with at least one UV absorber selected from the following: p-aminobenzoic acid (PABA), Padimate O, ensulizole, cinoxate, benzophenone-3, enzophenone-8, homosalate, meradimate, octocrylene, 2-ethylhexyl-p-methoxycinnamate, octyl salicylate, sulisobenzone, trolamine salicylate, avobenzone, ecamsule, titanium dioxide, zinc oxide, 4-methylbenzylidene, Tinosorb M, neo heliopan AP, mexoryl XL, benzophenone-9, Uvinul T150, Uvinul A Plus, Uvasorb HEB, Parsol SLX, and isopentenyl-4-methoxycinnamate.

Additionally, it will be recognized by one skilled in the art that tanning agents frequently contain one or more UV absorbers (typically at lower addition levels than found in sun blocks), along with moisturizers, emollients, and other adjuvants like fragrance.

By way of example, it was surprisingly discovered that bis-N-ethyl pyrrolidone ether possesses a high refractive index of (around 1.51), suggesting compositions for imparting high shine, such as rinse-off (e.g., shampoos and conditioners) and leave-in (e.g., sprays, mousses, and gels) hair care products. The inventive ethers of the present invention may partially or replace all of such cosmetic solvents with the benefits of improved performance, reduced irritation, better sensory aesthetics (like feel), and/or reduced interaction with other ingredients. Addition levels, coformulary ingredients, products, and product forms include those taught in research disclosures IPCOM 000128968D, available at http://priorartdatabase.com/IPCOM/000128968, and IPCOM 000109682D, available at http://priorartdatabase.com/IPCOM/000109682, both of which are incorporated herein their entirety by reference.

Pharmaceutical Compositions

Given sufficient purity, the ethers of the invention also find utility in pharmaceutical compositions for treating conditions affecting man or animal. The pharmaceutical compositions contain one or more pharmaceutical active ingredients ("drugs"). Highly preferably, the one or more pharmaceutical active ingredients remains chemically stable so that the active(s) remain in their intended chemical and/or crystalline (or amorphous) form without concerns of undue toxicity or loss of biological activity.

Suitable pharmaceutical forms include solids, semi-solids, liquids, tablets, powders, granules, lozenges, capsules, patches, ointments, powders, lotions, gels, creams, suppositories, suspensions, liposomes, and aerosols. Illustrative examples of liquid forms include syrups, elixirs, emulsions, sterile liquids (e.g., for injection), or a non-aqueous or aqueous liquid suspension. These forms may be delivered via oral, parenteral, topical (dermal), intravaginal, intranasal, intrabronchial, intraocular, intraaural, and/or rectal routes of administration. For oral administration, the pharmaceutical formulations may be utilized as e.g., tablets, capsules, emulsions, solutions, syrups or suspensions. For parenteral administration, the formulations may be utilized as ampoules, or otherwise as suspensions, solutions or emulsions in aqueous or oily vehicles.

Acceptable methods for preparing suitable pharmaceutical compositions having the ethers are known or may be routinely determined by those skilled in the art. For example, pharmaceutical preparations may be prepared following conventional techniques of the pharmaceutical chemist, involving steps such as mixing, granulating, and compressing, when necessary, for tablet forms, or mixing, filling, and dissolving the ingredients as appropriate.

Pharmaceutical compositions embraced by the invention also may include suitable excipients, diluents, vehicles, solubilizers, and surfactants, carriers, as well as other pharmaceutical active ingredients, depending upon the intended use. One such reference for identifying suitable excipients is *Pharmaceutical Excipients*, R. C. Rowe, et al. (eds.), Pharmaceutical Press and American Pharmaceutical Association, 2003, which is incorporated herein its entirety by reference. Solid or liquid pharmaceutically-acceptable carriers, diluents, vehicles, or excipients may be employed in the pharmaceutical compositions. Illustrative solid carriers include: starch, lactose, calcium sulfate damantin, poly (vinyl pyrrolidone), poly(vinyl pyrrolidone-co-vinyl acetate), terra alba, sucrose, talc, gelatin, pectin, acacia, magnesium stearate, and stearic acid. Illustrative liquid carriers include syrup, peanut oil, olive oil, saline solution, water, and ethanol. The carrier or diluent may include a suitable prolonged-release material such as glyceryl monostearate or glyceryl distearate, either alone or in combination with a wax.

Examples of suitable solubilizers include, without limitation: vitamin E substances (e.g., $\alpha$-, $\beta$-, $\gamma$-, $\delta$-, $\zeta_1$-, $\zeta_2$-, $\epsilon$-tocopherols, their dl, d and l forms and their structural analogues), monohydric alcohols (e.g., ethanol, 2-propanol, tert-butanol), phospholipids (e.g., phosphatidylcholine, phosphatidylethanolamine, phosphatidylserine, phosphatidylinositol, lecithins, lysolecithins, lysophosphatidylcholine, polyethylene glycolated phospholipids/lysophospholipids, lecithins/lysolecithins and mixtures thereof), glycerol fatter acid esters (e.g., monoglycerides, diglycerides, medium chain triglycerides with fatty acids having about 6-12 carbons and mixtures thereof), propylene glycol esters (e.g., propylene carbonate, propylene glycol monoacetate, propylene glycol diacetate, propylene glycol fatty acid esters, acetylated propylene glycol fatty acid esters and mixtures thereof), ethylene glycol esters (e.g., monoethylene glycol monoacetates, diethylene glycol esters, polyethylene glycol esters and mixtures thereof).

Examples of surfactants suitable for use in the present invention are disclosed in U.S. Pat. No. 6,294,192 and U.S. Pat. No. 6,267,985. Examples of surfactants that may be used in the present invention include polyethoxylated fatty acids such as PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate; PEG-fatty acid diesters such as PEG-20 dilaurate, PEG-20 dioleate, PEG-20 distearate, PEG-32 dilaurate and PEG-32 dioleate; PEG-fatty acid mono- and di-ester mixtures; polyethylene glycol glycerol fatty acid esters such as PEG-20 glyceryl laurate, PEG-30 glyceryl laurate, PEG-40 glyceryl laurate, PEG-20 glyceryl oleate, and PEG-30 glyceryl oleate; alcohol-oil transesterification products such as PEG-35 castor oil (Cremophor® RH40), polyoxyl 35 castor oil (Cremophor® EL), PEG-25 trioleate (TAGAT® TO), PEG-60 corn glycerides (Crovol® M70), PEG-60 almond oil (Crovol® A70), PEG-40 palm kernel oil (Crovol® PK70), PEG-50 castor oil (Emalex® C-50), PEG-50 hydrogenated castor oil (Emalex® HC-50), PEG-8 caprylic/capric glycerides (Labrasol®), and PEG-6 caprylic/capric glycerides (Softigen® 767); transesterification products of oils and alcohols; polyglycerized fatty acids such as polyglyceryl oleate (Plurol® Oleique), polyglyceryl-2 dioleate (Nikkol DGDO), and polyglyceryl-10 trioleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860); propylene glycol fatty acid esters such as propylene glycol monolaurate (Lauroglycol FCC), propylene glycol ricinoleate (Propymuls), propylene glycol monooleate (Myverol® P-06), propylene glycol dicaprylate/dicaprate (Captex® 200), and propylene glycol dioctanoate (Captex 800); mixtures of propylene glycol esters and glycerol esters such as a mixture of oleic acid esters of propylene glycol and glycerol (Arlacel 186); mono- and diglycerides such as glyceryl monooleate (Peceol), glyceryl ricinoleate, glyceryl laurate, glyceryl dilaurate (Capmul GDL), glyceryl dioleate (Capmul GDO), glyceryl mono/dioleate (Capmul GMO-K), glyceryl caprylate/caprate (Capmul MCM), caprylic acid mono/diglycerides (Imwitor® 988), and mono- and diacetylated monoglycerides (Myvacet® 9-45); sterol and sterol derivatives such as PEG-24 cholesterol ether (Solulan® C-24); polyethylene glycol sorbitan fatty acid esters such as PEG-20 sorbitan monolaurate (Tween® 20), PEG-20 sorbitan monopalmitate (Tween® 40), PEG-20 sorbitan monostearate (Tween® 60), and PEG-20 sorbitan monooleate (polysorbate 80 or Tween® 80); polyethylene glycol alkyl ethers such as PEG-3 oleyl ether (Volpo 3) and PEG-4 lauryl ether (Brij® 30); sugar esters such as sucrose monopalmitate and sucrose monolaurate; polyethylene glycol alkyl phenols; polyoxyethylene-polyoxypropylene block copolymers such as Synperonic® PE series (ICI); Pluronic® series (BASF), Emkalyx, Lutrol® (BASF), Supronic, Monolan, Pluracare®, and Plurodac®; sorbitan fatty acid esters such as sorbitan monolaurate (Arlacel® 20), sorbitan monopalmitate (Span-40), sorbitan monooleate (Span-80), sorbitan monostearate, and sorbitan tristearate; lower alcohol fatty acid esters such as hydrophobic surfactants include ethyl oleate (Crodamol EO), isopropyl myristate (Crodamol IPM), and isopropyl palmitate (Crodaimol IPP); ionic surfactants such as sodium oleate, sodium lauryl sulfate, sodium lauryl sarcosinate, sodium dioctyl sulfosuccinate, sodium cholate, sodium taurocholate, lauroyl carnitine, palmitoyl carnitine, and myristoyl carnitine; unionized ionizable surfactants such as free fatty acid, particularly C6-C22 fatty acids, and bile acids.

Other surfactants for use in the present invention include, without limitation, PEG-400 succinate, PEG 3350, tocopherol polyethylene glycol (molecular weight: 200-8000 g/mol) succinate, tocopherol polyethylene glycol 400 succinate, tocopherol polyethylene glycol 1000 succinate (Vitamin E-TPGS, Eastman Chemical Co.), glycerol monolinoleate (Maisine®), propylene glycol monocaprylate (Capryol® 90); caprylocaproyl macrogol-8 glycerides (Labrosol®), glycerol dibehenate (Compritol® 888), glycerol distearate (Precirol®), lauroyl macrogol-32 glycerides (Gelucire® 44/14), and stearoyl macrogol-32 glycerides (Gelucire 50/13).

Uses of the Ethers

Ethers described here find utility in various performance chemicals, personal care, and pharmaceutical applications. To better understand the utility embraced by the invention, each application art is described separately.

Performance Chemicals Use

In performance chemicals applications, the present invention provides an assorted variety of uses. Especially preferred is the use of the ethers in freezing point depressors, solvents/solubilizers, gas hydrate inhibitors, anti-agglomerants, printing inks/dyes, batteries, print strippers, separating polyunsaturated oils, cleaning, bird and insect repellents, crop protection, slimacides, fungicides, and coatings. Illustrations of these uses are provided in the Examples section.

As described earlier, blends of bis-N-ethyl pyrrolidone ether and water were found to exhibit surprisingly low freezing points, as result that indicates usage as an anti-freeze. This use is not limited to maintaining the operability of engines in cold weather, but extends to all such uses where composition freezing is undesired. Preferred is the use of one or more ethers as an anti-freeze in combination with water or when used in water-containing environments. Examples include the use of the ether(s): as an anti-freeze on the exterior surfaces (windshields, windows, mirrors, moving parts) of transportation equipment (airplanes, automobiles, trains, ships), as an anti-icing additive to fuels like gasoline, as a protectant for crops from freezing, and as an anti-freeze for pipelines. Also included are the uses of the ethers, alone or in combination with water or other compounds, in biocides, slimacides, fungicides, paints, caulks, putties, sealing compounds, and cleaning agents.

Significantly, ethers of the invention may serve as solvents, performing in compositions as summarized above and in the Examples section. The uses range from paint strippers, to cleaning solvents for hard surfaces, engine parts, and as an extraction solvent (e.g., for the absorption of sulfurous compounds, carbon dioxide, carbon monoxide, and the separation of saturated and unsaturated oil components). Contemplated is the use of the ether(s) as a solvent, especially reactions benefitting from the high thermal decomposition and boiling point, as well as reaction benefitting from a catalytic solvent (e.g., polymerization solvent for polymers (e.g., condensation polymers like imides and addition polymer involving vinylation) and as a reaction solvent for methylene bis-thiocyanate and related compounds). Also included is the use of the ethers in the manufacture of lubricating oils. Especially preferred is the use of the ether(s) as a partial or complete replacement for solvents having a lesser safety profile, which includes solvents like N-methyl-2-pyrrolidone, halogenated solvents, and aromatic solvents, including those mentioned in the earlier section on compositions.

Also discovered was the use of the ethers as a gas hydrate inhibitor and anti-agglomerant. At addition levels of 0.5% (w/w) and 1.0% (w/w), bis-N-ethyl pyrrolidone ether use considerably limited gas hydrate formation, as those that did form at a pressure of 123 bars and 2.8° C. were miniscule and well dispersed. This combination of performance indicates the ether provides both hydrate inhibition and anti-agglomerant benefits.

The ethers of the invention also may be used for cleaning, where they are used for cleaning metal parts, electronic and computer components, carburetors and other engine cleaning, and may be used for oxidative cleaning with peroxides. As a cleaner, the ethers also find application in removing stains from fabrics, upholsteries, carpets, as well as impervious surfaces like plastics and tiles. Its use in soaps and detergents is contemplated. The ethers also provide stripping action, removing and/or listing polymerics from electronic assemblies, removing epoxy smears, loose fibers, soldering residues, insulating lacquers and cured siloxane coatings. An example describes paint stripping compositions and its uses for partially or completely removing paints and graffiti.

Additionally, the ethers described herein may serve in photoresist technologies as a component in developing solutions by stripping the exposed resists, and as a coalescing agent for poly(chloroprene) emulsions.

Personal Care (Cosmetic) Use

As ethers of sufficient purity, especially bis-N-ethyl pyrrolidone ether, are believed to possess a benign safety profile, the use of these compounds in personal care (cosmetic) compositions is contemplated. In particular, uses on the skin, hair, and nails are within the scope of the invention. Especially preferred is the use of the ethers to remove make-up and nail polish. Other uses of the ethers in personal care compositions are included in research disclosures IPCOM 000128968D, available at http://priorartdatabase.com/IPCOM/000128968, and IPCOM 000109682D, available at http://priorartdatabase.com/IPCOM/000109682, both of which are incorporated herein their entirety by reference.

Pharmaceutical Use

Pharmaceutical uses of the ethers of the instant invention may find usefulness as solubilizers, bioenhancement aides, and penetration enhancers in pharmaceuticals.

The invention will now be described with reference to the following examples:

EXAMPLES

Example 1

Physical Properties of Bis-N-Ethyl Pyrrolidone Ether

Eleven physical properties were measured of bis-N-ethyl pyrrolidone ether (neat) (Table 1). These properties reveal the substantial, low freezing point of the ether, an extremely high boiling point, high thermal stability, and a static surface tension that is less than water.

TABLE 1

Measured physical properties of bis-N-ethyl pyrrolidone

| property | value |
| --- | --- |
| physical state | liquid (ambient conditions) |
| boiling point | not determined up to 175° C. |
| | >350° C. at 1 atm, from distillation |
| freezing point | <−80° C. |
| thermal decomposition temperature | 275° C. |
| pH in a 50% aqueous solution | 9.5 |
| color (APHA) | >500 |
| refractive index | 1.5063 |
| specific gravity | 1.148 |
| viscosity | 156 cP-176 cP* |
| | 96.4 cP† |
| surface tension (static) | 51.1 dynes/cm² (ring) |
| | 50.2 dynes/cm² (plate) |

*Brookfield RV viscometer, #2 spindle, 10 rpm
†Cannon Fenske viscometer, #300 tube

Example 2

Aqueous Behavior of Bis-N-Ethyl Pyrrolidone Ether

Blends of bis-N-ethyl pyrrolidone ether were made with water in an equal mass ratio. The blends were pH adjusted from 1 to 13 and then chilled to −15° C. At no point did any blend exhibit two-phase behavior, as only a single phase was ever produced.

Example 3

Solvent Miscibility Studies of Bis-N-Ethyl Pyrrolidone Ether Blends

Blends of bis-N-ethyl pyrrolidone ether were made with nine solvents in equal volume ratio (Table 2). The blends were visually observed to determine miscibility of the ether with the various solvents. It was discovered that bis-N-ethyl pyrrolidone ether is miscible with water, methanol, 2-propanol, acetone, methyl ethyl ketone, ethyl acetate, and toluene. However, in this ratio the ether is immiscible with hexane and cyclohexane.

TABLE 2

Measured physical properties of bis-N-ethyl pyrrolidone

| solvent | observation |
| --- | --- |
| water | miscible |
| methanol | miscible |
| 2-propanol | miscible |
| acetone | miscible |
| methyl ethyl ketone | miscible |
| ethyl acetate | miscible |
| toluene | miscible |
| hexane | insoluble |
| cyclohexane | insoluble |

Example 4

Freezing-point Depression of Bis-N-ethyl Pyrrolidone Ether/Water Blends

The freezing points of bis-N-ethyl pyrrolidone ether/water blends were measured using differential scanning calorimetry. All measurements were conducted under nitrogen purge from 25° C. to −80° C. at a cooling rate of 5° C./min using a $Q_{2000}$ calorimeter by TA Instruments.

Freezing depressions were measured for bis-N-ethyl pyrrolidone ether/water blends (Table 3). Notably, the bis-N-ethyl pyrrolidone ether/water blend in equal weight ratio exhibited a freezing point of −43.2° C., markedly lower than the reported freezing point value of −32° C. for ethylene glycol and water in equal mass ratio (Table 4).

TABLE 3

Freezing points for bis-N-ethyl pyrrolidone ether/water blends and ethylene glycol/water blends.

| bis-N-ethyl pyrrolidone ether (by mass) | freezing point (° C.) |
| --- | --- |
| 1% in water | −9.3 |
| 5% in water | −7.9 |
| 10% in water | −13.5 |
| 20% in water | −13.3 |
| 30% in water | −18.2 |
| 40% in water | −28.6 |
| 50% in water | −43.2 |
| 60% in water | <−80 |
| 66% in water | <−80 |
| 75% in water | <−80 |
| 100% bis-N-ethyl pyrrolidone ether | <−80 |

TABLE 4

Freezing points for ethylene glycol/water blends (from www.engineeringtoolbox.com).

| ethylene glycol (by mass) | freezing point (° C.) |
| --- | --- |
| 0% in water | 0 |
| 11% in water | −3 |
| 22% in water | −8 |
| 32% in water | −16 |
| 43% in water | −25 |
| 53% in water | −37 |
| 63% in water | −55 |

Example 5

Enhanced Freezing Point Depression of Water-Glycerol Mixtures with Added Bis-N-ethyl Pyrrolidone Ether Different binary blends of glycerol and water are prepared, and then bis-N-ethyl pyrrolidone ether is added in 1% increments from 0% to 50% of the ether. The freezing point depression of these compositions is measured using a suitable differential thermometer (e.g., a thermocouple).

The addition of bis-N-ethyl pyrrolidone ether is found to further depress the freezing point depression compared to the glycerol-water binary blends.

Example 6

Enhanced Freezing Point Depression of Eutectic Blend of Glycerol-Water Blend with Added Bis-N-ethyl Pyrrolidone Ether As a specific subclass to Example 5, a eutectic blend of glycerol-water is prepared, having about 65% glycerol (by weight) and a freezing point depression of about −46° C. Bis-N-ethyl pyrrolidone ether is added in 1% increments from 0% to 50% added ether. The freezing point depression of these compositions is measured using a suitable differential thermometer (e.g., a thermocouple).

A freezing point depression lower than about −46° C. is found.

Example 7

Enhanced Freezing Point Depression of Other Blends

Example 5 and 5 are repeated, replacing glycerol with ethylene glycol, propylene glycol, or pentaerythritol.

The addition of bis-N-ethyl pyrrolidone ether lowers the freezing point depression compared to solutions without the ether.

Example 8

Use of Enhanced Freezing Point Depression Compositions

The compositions of Examples 4-7 are found to be effective deicers, especially for the exterior surfaces (e.g., windshields, windows, wings, equipment) of transportation vehicles (e.g., airplanes, cars, trains) and for road surfaces. These compositions also may be used as a radiator fluid, and other applications requiring a depression of water freezing point.

Example 9

Polymer Compatibility with Bis-N-Ethyl Pyrrolidone Ether

Two studies were completed to assess the compatibility of seven polymers (in powder form) with bis-N-ethyl pyrrolidone ether. In the first study a dispersion was prepared of each polymer at 10% addition level (w/w solvent) at ambient temperature (about 25° C.). For the second study dispersions of each polymer at 5% addition (w/w) were maintained at 200° C. for 24 hours, and then cooled to ambient.

The results indicate bis-N-ethyl pyrrolidone ether solubilizes PVP at room temperature (Table 5), supporting the proposal to employ the ether in pharmaceutical medicaments, PVP-iodine complexes, soaps and scrubs, binders of various sorts, glue sticks, hot melts, batteries, inks, photoresists, metal quenching compounds, membranes, and anti-recrystallization agents to name a few. The heat-enabled solubilities of poly(vinylidene fluoride) in the ether suggest the use of this solvent in wire coating productions, electrically-insulating coatings, UV-resistant films, metal coatings, and halogen-resistant films and coatings. Similarly, the identified solubility of poly(sulfone) proposes the use of this ether in chemically-resistant films and coatings, and in the production/processing of flame retardant devices, medical instrument and equipment, waste water treatment, food and beverage processing, membranes, dielectrics, and filtration media. The ether's solvent miscibility can be advantageously exploited to help solubilize other polymers, e.g., alkylated poly(vinyl pyrrolidone) in a blend of bis-N-ethyl pyrrolidone ether and cosmetic oils. Bis-N-ethyl pyrrolidone ether also may serve as a plasticizer for PVC, which swelled when stored in the ether.

TABLE 5

Polymer compatibility with bis-N-ethyl pyrrolidone ether

| polymer | study 1 (10% solids @ ambient, 1 week) | study 2 (5% solids) 200° C. (24 hours) | study 2 (5% solids) cooled to ambient |
|---|---|---|---|
| poly(butene terephthalate) | insoluble | soluble | precipitation forms |
| poly(phenylene sulfide) | insoluble | insoluble | NAv |
| poly(vinylidine fluoride) | insoluble | soluble | soluble |
| poly(sulfone) | mostly insoluble | soluble | soluble |
| poly(vinyl chloride) | partly soluble/swollen | black precipitation forms | black precipitation forms |
| poly(vinyl pyrrolidone) (PVP K-29/32) | soluble | NAv | NAv |
| C20 alkylated poly(vinyl pyrrolidone) (Ganex ® V-220) | insoluble (dispersion) | insoluble (dispersion) | insoluble (dispersion) |

Example 10

Use In Electronic Circuit Board Cleaning

Bis-N-ethyl pyrrolidone ether is used to clean electronic circuit boards, including the removal of fluxing agents, polymer agents, plastic potting compositions, epoxy smears, loose fibers, soldering residues, insulating lacquers, and cured siloxane coatings. Additional ingredients, may be included to enhance the cleaning performance including, but not limited to, peroxides.

The ether also is used for cleaning and degreasing silicon wafers for integrated circuits.

Example 11

Use as Examination Fluids for Metal Surfaces and Boards

Bis-N-ethyl pyrrolidone ether also is effective for formulating examination fluids for non-destructive inspection of metal surfaces and metal boards. Dyes and/or brighteners may be dissolved in the ether for this use.

Example 12

Battery Compositions and Uses Thereof

A lithium-nickel halide battery is produced having an electrolyte solvent that comprises bis-N-ethyl pyrrolidone ether. Similar type batteries include lithium sulfur dioxide and standard silver-silver chloride batteries.

The batteries exhibit enhanced low temperature performance, e.g., at temperatures of 100° C. or less.

Example 13

Use as a Print Solvent

Bis-N-ethyl pyrrolidone ether is used to clean printing equipment, such as printing screens and printing surfaces. Such formulations may consist almost essentially of the ether. Other cleaning agents may be included with the ether to enhance surfactancy, wetability, and/or solvency, especially additives known to be useful for cleaning printing equipment.

Bis-N-ethyl pyrrolidone ether-based formulations also may be used to dissolve coating resist layers.

Bis-N-ethyl pyrrolidone ether also may be used as a solvent for developing the image by stripping the exposed resists. The solvent develops exposed resists by dissolving the exposed areas to produce positive image or by dissolving unexposed area producing negative image.

Some of the resist coating polymeric precursors are solutions of polyamic acids to produce: polyimides, polyamide esters, polyaryl sulfones, polymethacrylic anhydrides and polychloroprene emulsion (coalescing agent).

Example 14

Use as Polymerization Reaction Solvent

Bis-N-ethyl pyrrolidone ether is used as a reaction solvent for halogenated polymers, especially chloropolymers, with salts of unsaturated acids like cinnamic acid, to produce radiation-sensitive polymers.

Example 15

Use as a Reaction Solvent for Methylene Bis-thiocyanate

A reaction between methylene dibromide and sodium thiocyanate is performed by dissolving one mole of methylene dibromide for every two moles of sodium thiocyanate in 2-5 moles of bis-N-ethyl pyrrolidone ether. The composition is blanketed under nitrogen and heated for a period of 8 hours, and the reaction is completed as indicated by the absence of unreacted methylene dibromide and the precipitation of sodium bromide. Sodium bromide is removed from the reaction product, methylene bis-thiocyanate, by filtration.

Example 16

Use as a Cleaner to Remove Carbon Deposits

Bis-N-ethyl pyrrolidone ether is used to clean equipment having carbon deposits, including, but not limited to internal combustion engines and parts like carburetors, valves, pistons, cylinder heads and chambers. The ether can be applied into an idling engine optionally with a cosolvent like an engine fuel or ethanol, or, can also be used with disassembled engine parts. Additionally, bis-N-ethyl pyrrolidone ether can remove grease from engine parts.

Example 17

Use in Sour Gas Cleaning

Sour gas, being any gas having significant amounts of hydrogen sulfide, is cleaned using bis-N-ethyl pyrrolidone ether using a scrubbing process. Bis-N-ethyl pyrrolidone ether catalytically decomposes carbon oxysulfide to carbon dioxide and water, and extracts hydrogen sulfide. An advantage to this method over conventional alkali washing is that it does not consume the carbon dioxide.

Example 18

Use as an Extractive Solvent to Absorb Flue Gases

Bis-N-ethyl pyrrolidone ether is employed as an extractive solvent for the removal of chlorinated compounds, such as vinyl chloride, 1,2-dichloroethane, and 1,1-difluoroethane, e.g., from production operations. In addition, polar organic compounds like acrolein and acetonitrile also can be separated by use of this extractive solvent.

Example 19

Use in the Production of Lubricating Oils

Impurities in petroleum fraction are removed by using bis-N-ethyl pyrrolidone ether as a solvent, producing the corresponding, high quality lubricating oil. Advantages to this approach may include: cost saving, energy efficiency, higher yield, improved product composition, operation stability, safety, or less equipment corrosion.

Example 20

Use of Bis-N-ethyl Pyrrolidone Ether as a Gas Hydrate Inhibitor and/or Anti-Agglomerant Bis-N-ethyl pyrrolidone ether was assessed as a gas hydrate inhibitor and as an anti-agglomerant. A three-part fluid blend was prepared having equal mass amounts of Troika crude oil (black oil), synthetic condensate, and a sodium chloride brine solution into which the ether was dissolved. Ether addition levels were studied two times at 0.5% (w/w NaCl brine solution), and one time at 1.0% (w/w NaCl brine solution). The abovementioned fluid blend blanketed with Green Canyon gas (Table 6) at a pressure of 123 bar and maintained at 2.8° C. for the tests.

In each test the formation of gas hydrates and agglomerants was surprisingly very small. Those hydrates and agglomerants that did form remained very small and very well dispersed through the fluid blend.

TABLE 6

| Green Canyon gas composition | |
|---|---|
| component | amount (molar percent) |
| nitrogen | 0.39 |
| methane | 87.26 |

TABLE 6-continued

Green Canyon gas composition

| component | amount (molar percent) |
|---|---|
| ethane | 7.57 |
| propane | 3.10 |
| iso-butane | 0.49 |
| N-butane | 0.79 |
| iso-pentane | 0.20 |
| N-pentane | 0.20 |
| total | 100.00 |

Example 21

Use in Oilfield Applications

Bis-N-ethyl pyrrolidone ether also finds useful application as a partial or total replacement for gas hydrate inhibition delivery fluid.

Example 22

Paint Stripping Formulas and Uses Thereof

Paint stripping formulas are prepared containing bis-N-ethyl pyrrolidone ether (Table 7). Their paint stripping efficacies are evaluated using different grades of paint and varnish from pine and maple wood substrates.

The paint stripping formulations are effective in removing dried cured paints and varnishes.

TABLE 7

Paint stripping formulations of Example 22

| ingredient | mass addition range | preferable mass range |
|---|---|---|
| bis-N-ethyl pyrrolidone ether | 10-80% | 40-60% |
| gamma butyrolactone | 10-80% | 40-60% |
| ethoxy ethyl propionate | 1-10% | 3-8% |
| thickener agent (e.g., hydroxypropyl cellulose, Klucel ® H[1]) | 0.3-2% | 0.5-1.5% (depends on desired viscosity) |
| bittering agent (diatonium) | 10-100 ppm | |

[1]Ashland Inc.

Example 23

Ink Formulations for Uses Thereof

High-speed jet printing inks are formulated with bis-N-ethyl pyrrolidone ether to create inks that are light-fast, non-clogging, and water-thinning.

Such inks may be used for non-porous surfaces like ceramics, plastics, and poly(vinyl butyral) sheets used for laminated windshields.

Example 24

Pigment Formulations and Uses Thereof

Pigments are formulated with bis-N-ethyl pyrrolidone ether, e.g., at 1% addition with respect to pigment mass, to reduce grinding energy, produce fine pigments with increased tinctorial strength, increase stability against flocculation and settling. Especially preferred pigments include diazo compounds, phthalocyanines, isoindolinones, and quinacridones.

Pigments formulated with bis-N-ethyl pyrrolidone ether can improve the dyeing of polyester- and polyamide-based substrates, e.g., fabrics, via swelling of the fibers during the dyeing process.

Example 25

Compositions for the Separation of Polyunsaturated Oils and Uses Thereof

A blend of bis-N-ethyl pyrrolidone ether and ethylene glycol with optional glycerol is prepared to separate and recover a solvent layer enriched in the polyunsaturated fraction of natural oils from the saturated fraction using the extraction process/fractionation.

Example 26

Matrix Composition #1

A 100 g matrix composition is prepared by combining the ingredients of Table 8 in 2-ounce stoppered bottle.

The composition is homogeneous.

TABLE 8

Matrix composition #1 of Example 26

| ingredient | mass (g) |
|---|---|
| bis-N-ethyl pyrrolidone ether | 12.5 |
| ethoxylated castor oil (30EO) | 74.5 |
| poly(EO/PO/EO) (Pegol ® L-31[1]) | 11.0 |
| branched ethoxylated phosphate ester (9-10 EO) | 2.0 |
| total | 100.0 |

[1]Rhodia

Example 27

Matrix Composition #2

A mixture is prepared by combining matrix composition #1 with reduced vinyl pyrrolidone dimer (Table 9) in a 2-ounce stoppered bottle.

A homogeneous solution of the desired matrix composition is produced.

TABLE 9

Matrix composition #2 of Example 27

| ingredient | mass (g) |
|---|---|
| matrix composition #1 | 88 |
| reduced vinyl pyrrolidone dimer (RVPD)[1] | 12 |
| total | 100 |

[1]International Specialty Products

Example 28

Matrix Composition #3

A mixture is prepared by combining matrix composition #1 with N-octyl pyrrolidone (Table 10) in a 2-ounce stoppered bottle.

A homogeneous solution of the desired matrix composition is produced.

TABLE 10

| Matrix composition #3 of Example 28 | |
|---|---|
| ingredient | mass (g) |
| matrix composition #1 | 88 |
| N-octyl pyrrolidone[1] | 12 |
| total | 100 |

[1]International Specialty Products

Example 29

Matrix Composition #4

A mixture is prepared by combining matrix composition #1 with mixture of N,N-dimethyl octanamide and N,N-dimethyl decanamide (Table 11) in a 2-ounce stoppered bottle.

A homogeneous solution of the desired matrix composition is produced.

TABLE 11

| Matrix composition #4 of Example 29 | |
|---|---|
| ingredient | mass (g) |
| matrix composition #1 | 88 |
| mixture of N,N-dimethyl octanamide and N,N-dimethyl decanamide (Halcomid ® M 8-10)[1] | 12 |
| total | 100 |

[1]Stepan Corp.

Example 30

Matrix Composition #5

Matrix composition #5 is formed by dissolving 28 g of hexyl acetate in 72 g of matrix composition #1. Diluted solutions of 1/10, 1/100 and 1/1000 are clear.

Active ingredients that exhibit solubility in hexyl acetate can be formulated using the matrix composition #5.

Example 31

Matrix Composition #6

Example 30 is repeated except 50 g of hexyl acetate is dissolved in 50 g of matrix composition #1. Diluted solutions of 1/100 and 1/1000 are clear upon preparation.

Example 32

Matrix Composition #7

A mixture is prepared by combining the ingredients of Table 12 in a 2-ounce stoppered bottle at ambient temperature.

Samples were diluted using the method described in Example 30, and dilutions of 1/100 and 1/1000 are clear upon preparation.

TABLE 12

| Matrix composition #7 of Example 32 | |
|---|---|
| ingredient | mass (g) |
| matrix composition #1 | 80 |
| dipentene[1] | 20 |
| total | 100 |

[1]Sigma Aldrich

Example 33

Matrix Composition #8

A mixture is prepared by combining the ingredients of Table 13 in a 2-ounce stoppered bottle.

Diluted solutions of 1/10, 1/100 and 1/1000 are clear upon preparation.

TABLE 13

| Matrix composition #8 of Example 33 | |
|---|---|
| ingredient | mass (g) |
| matrix composition #1 | 80 |
| benzyl benzoate[1] | 20 |
| total | 100 |

[1]Sigma Aldrich

Example 34

Matrix Composition #9

A mixture is prepared by combining the ingredients of Table 14 in a 2-ounce stoppered bottle.

Diluted solutions of 1/10, 1/100 and 1/1000 are clear upon preparation.

TABLE 14

| Matrix composition #9 of Example 34 | |
|---|---|
| ingredient | mass (g) |
| matrix composition #1 | 90 |
| methyl methacrylate[1] | 10 |
| total | 100 |

[1]Dow Chemical

Example 35

Matrix Composition #10

A mixture is prepared by combining the ingredients of Table 15 in a 2-ounce stoppered bottle.

This concentrate is diluted to 1/100 and 1/1000 and dilutions of 1/100 and 1/1000 are clear upon preparation.

TABLE 15

Matrix composition #10 of Example 35

| ingredient | mass (g) |
|---|---|
| matrix composition #1 | 70 |
| ethyl caprylate | 30 |
| total | 100 |

Example 36

Preparations with 20% Pine Oil

Two pine oil preparations are prepared containing the ingredients and addition levels indicated in Table 16. The pine oil preparations are transferred onto a rotary wheel for overnight mixing. The resulting formulations are clear solutions. Then, these concentrated compositions are diluted with deionized water to various dilutions (from 1/8 to 1/16 ratio) and produce optically clear compositions. Diluted samples are placed on a rotary wheel for 20 minutes prior to haze measurement. Haze measurements are made using a Hatch 2100N Turbidity meter. At dilution ratio of 1/4 and higher all the both formulations are clear and flowable with turbidity measurements of about 5 NTU or less.

The preparations exhibit biodegradability and suggests their use in contact with plants, animals, or humans, such as cleaning compositions, crop protection, safeners for crops, and carriers for leaf wetting.

TABLE 16

Preparations with 20% pine oil of Example 36

| ingredient | concentration |
|---|---|
| pine oil | 20.0% |
| dioctyl sulfosuccinate sodium salt[1] (DOSS) | 13.3% |
| matrix composition #3 or #4 | 66.6% |
| total | 100.0% |

[1]Cytec Industries, Inc.

Example 37

Preparations with 43% Pine Oil

A 43% by weight solution of pine oil is prepared by weighing 22 grams of pine oil, 6.5 gram of DOSS, and 22.5 grams of matrix compositions #3 or #4 (Table 17). Concentrates are transferred onto a rotary wheel for overnight mixing. The concentrates are diluted with deionized water to various dilutions from 1/8 to 1/64 ratio and found to be optically clear.

As with the preparations from Example 36, these formulations having a higher concentration of pine oil may be used for cleaning formulas and the mentioned agricultural applications.

TABLE 17

Concentrated composition of Example 37

| ingredient | concentration |
|---|---|
| pine oil | 43.1% |
| DOSS[1] | 12.7% |
| matrix composition #3 or #4 | 44.2% |
| total | 100.0% |

[1]Cytec Industries, Inc.

Example 38

Stain Removal Formulas #1 and #2 and Uses Thereof

The two stain removal formulas shown in Table 18 are made by charging the ingredients, first water followed by the other components in the order shown, and stirring suitably by a mechanical device until homogeneous product is obtained. The stain removal formulas #1 and #2 are tested along with commercial laundry stain remover from cotton polyester pre-stained from Scientific Services (Oakland, N.J.). The stain removing formulas are applied by spotting on the pre-stained swatches for 1 or 15 minutes then washing with warm tap water (time between application and washing is designated Δt). Performance is judged by visual inspection by three independent judges as per ASTM 4265-83.

Stain removal formulas #1 and #2 remove many of the standard stains better the commercial formula (Table 19).

TABLE 18

Laundry pre-wash/spot and stain remover compositions

| | mass percent | |
|---|---|---|
| ingredient | formula #1 | formula #2 |
| water | 53.2 | 71.2 |
| bis-N-ethyl pyrrolidone ether | 10.0 | 10.0 |
| BLO ® Solvent (ISP) | 10.0 | 10.0 |
| dodecyl benzene sulfonic acid[1] | 1.0 | — |
| Rhodafac ® RA-600[2] | 3.0 | 3.0 |
| Nekol ® WT-27[2] | — | 2.0 |
| Surfadone ® LP-100 (ISP) | 2.0 | — |
| ammonium hydroxide (as 100% NH$_3$) | 1.8 | 1.8 |
| triethanolamine | 2.0 | — |
| tetrapotassium pyrophosphate | 2.0 | — |
| trisodium phosphate | — | 2.0 |
| citric acid | 5.0 | — |
| propylene glycol | 10.0 | — |

[1]Pilot Chemicals,
[2]Rhone-Poulenc

TABLE 19

Laundry pre-wash/spot and stain remover evaluation results

| | % stain Removal | | | |
|---|---|---|---|---|
| | Δt = 15 min | | Δt = 1 min | |
| stain | formula #1 | commercial formula | formula #2 | commercial formula |
| wine | 95 | 65 | 95 | 30 |
| grass | 95 | 70 | 90 | 20 |
| coffee | 100 | 85 | 100 | 30 |
| spaghetti | 75-80 | 85 | 75 | 40 |

TABLE 19-continued

Laundry pre-wash/spot and stain remover evaluation results

| | % stain Removal | | | |
|---|---|---|---|---|
| | Δt = 15 min | | Δt = 1 min | |
| stain | formula #1 | commercial formula | formula #2 | commercial formula |
| chocolate | 30 | 15-20 | 5-10 | 10 |
| cosmetic makeup | 85 | 40-50 | 65 | 20 |
| motor oil | 10 | 5-10 | 5 | 5 |
| dust/sebum (cotton) | 20 | 0 | 20 | 20 |
| blood | 10 | 5 | 15 | 0 |
| lipstick (cotton) | 30 | 40 | 15 | 0 |

Example 39

Bird and/or Insect Repellent Formulas and Uses Thereof

Water-based formulations are made with bis-N-ethyl pyrrolidone ether and having a bird and/or insect repellent agents. Bird repellent formulations, which may contain conventional bird repellant ingredients like 1,2-butylene oxide, crystalline silica, and/or ethyl alcohol. Insect repellent formulations may include conventional insect repellent agents, like N,N-diethyl-m-toluamide (DEET), lemon eucalyptus essential oil, p-menthane-3,8-diol, icaridin, nepetalactone, citronella oil, neem oil, and/or bog myrtle. Either of these formulations may be applied as caulks, gels, wipes, lotions, or sprays. Especially preferred are bird and/or repellent formulations for use on or near building entrances, building fresh air in-take or exhaust, building ledges and alcoves, airports and surrounding grounds, and airplanes. Also especially preferred are insect formulations for topical application.

The formulations are found to be effective in preventing birds and/or insects from landing, walking, gathering, or feeding on or near treated surfaces and/or areas.

Example 40

Bird and/or Bat Cleaning Formulations and Uses Thereof

Water-based formulations having cleaning agents for bird and/or bat droppings are made with bis-N-ethyl pyrrolidone ether. The formulations may contain conventional materials to clean and/or sanitize bird droppings, such as octyl dectyl dimethyl ammonium chloride, sodium metasilicate, and dioctyl dimethyl ammonium chloride along with customary amount of detergent. The formulations can be applied as sprays or foams to windows and windshields to cleanse them from bird and/or bat dropping, saturating them prior to removal. Optionally, surfactants can be added to assist solubilizing hydrophobic material.

Example 41

Food-Grade Cleaning Formula and Use Thereof

A food-grade cleaning formula is prepared containing a blend of N,N-dimethyloctanamide (N,N-dimethylcaprylamide) and N,N-dimethyldecanamide (N,N-dimethylcapramide), sold into commercial trade under the name Hallcomid® M-8-10 by Stepan Company (Northfield, Ill.). The cleaning formula also contains food-grade non-ionic and anionic emulsifiers (Table 20). This composition is diluted with water in the range 1/50 to 1/200, producing stable emulsions without phase separation or crystal formation.

The diluted formula is effective to remove residual pesticide, fertilizers, and dirt from produce.

TABLE 20

Food-grade cleaning formulation of Example 41

| ingredient | mass percent | preferable mass percent |
|---|---|---|
| bis-N-ethyl pyrrolidone ether | 10%-90% | 20%-50% |
| Hallcomid ® M-8-10 | 10%-90% | 20%-50% |
| Bomol 4N or similar vegetable oil derived anionically modified[1] | 10%-90% | 20%-50% |
| Optimized combination of food-grade surfactant | 5%-10% | |

[1]International Specialty Products

Example 42

Permethrin Formula #1

Permethrin formula #1 is prepared by combining matrix composition #3 with permethrin, a broad spectrum insecticide, acaricide, and insecticide (Table 21) in a 2-ounce stoppered bottle.

TABLE 21

Permethrin formula #1 of Example 42

| ingredient | mass (g) |
|---|---|
| matrix composition #3 | 80 |
| permethrin | 20 |
| total | 100 |

Example 43

Permethrin Formula #2

Permethrin formula #2 is prepared by combining matrix composition #4 with permethrin, a broad spectrum insecticide, acaricide, and insect repellent (Table 22) in a 2-ounce stoppered bottle.

TABLE 22

Permethrin formula #2 of Example 43

| ingredient | mass (g) |
|---|---|
| matrix composition #4 | 80 |
| permethrin | 20 |
| total | 100 |

Example 44

Freeze/Thaw Stability of Permethrin Formulas

The freeze-thaw stability of permethrin formulas #1 and #2 are tested by storing the samples for three weeks at 0° C. and 50° C.

All samples pass standard freeze thaw cycle three times of alternate storage at 50° C. and 0° C. through room temperature for 24 hours at each temperature without any separation.

Example 45

Dilution Stability of Permethrin Formulas #1 and #2

The dilution stabilities of permethrin formulas #1 and #2 are tested as-is (undiluted) and after diluting them with either deionized water or WHO-defined 1000 ppm hard water at the dilution rates of 1/10, 1/100, and 1/1000. Samples were stored at ambient temperature (about 22° C.), sub-ambient temperature (4° C.), and elevated temperature (45° C.) conditions. A visual observation of stability was made, noting any phase separation or precipitation (ppt). Results are summarized in Tables 23, 24 and 25.

All samples stored at the ambient and sub-ambient temperature conditions remain clear after 100 days of storage. Nearly all samples stored at the elevated temperature condition remain clear after 100 days of storage. Samples at the 1/10 dilution rate precipitate after 15 days.

TABLE 23

Dilution stability of permethrin samples at about 22° C.

| day | dilution | permethrin formula #1 | #2 |
|---|---|---|---|
| 1 | none (as-is) | clear | clear |
|  | 1/10 | clear | clear |
|  | 1/100 | clear | clear |
|  | 1/1000 | clear | clear |
| 15 | none (as-is) | clear | clear |
|  | 1/10 | clear | clear |
|  | 1/100 | clear | clear |
|  | 1/1000 | clear | clear |
| 30 | none (as-is) | clear | clear |
|  | 1/10 | clear | clear |
|  | 1/100 | clear | clear |
|  | 1/1000 | clear | clear |
| 100 | none (as-is) | clear | clear |
|  | 1/10 | clear | clear |
|  | 1/100 | clear | clear |
|  | 1/1000 | clear | clear |

TABLE 24

Dilution stability of permethrin samples at 4° C.

| day | dilution | permethrin formula #1 | #2 |
|---|---|---|---|
| 1 | none (as-is) | clear | clear |
|  | 1/10 | clear | clear |
|  | 1/100 | clear | clear |
|  | 1/1000 | clear | clear |
| 15 | none (as-is) | clear | clear |
|  | 1/10 | clear | clear |
|  | 1/100 | clear | clear |
|  | 1/1000 | clear | clear |
| 30 | none (as-is) | clear | clear |
|  | 1/10 | clear | clear |
|  | 1/100 | clear | clear |
|  | 1/1000 | clear | clear |
| 100 | none (as-is) | clear | clear |
|  | 1/10 | clear | clear |
|  | 1/100 | clear | clear |
|  | 1/1000 | clear | clear |

TABLE 25

Dilution stability of permethrin samples at 45° C.

| day | dilution | permethrin formula #1 | #2 |
|---|---|---|---|
| 1 | none (as-is) | clear | clear |
|  | 1/10 | clear | clear |
|  | 1/100 | clear | clear |
|  | 1/1000 | clear | clear |
| 15 | none (as-is) | clear | clear |
|  | 1/10 | clear | ppts |
|  | 1/100 | clear | clear |
|  | 1/1000 | clear | clear |
| 30 | none (as-is) | clear | clear |
|  | 1/10 | clear | ppts |
|  | 1/100 | clear | clear |
|  | 1/1000 | clear | clear |
| 100 | none (as-is) | clear | clear |
|  | 1/10 | clear | ppts |
|  | 1/100 | clear | clear |
|  | 1/1000 | clear | clear |

Results of this example illustrate that active ingredients soluble in N-octyl pyrrolidone and/or Hallcomid® along with matrix compositions can be formulated as a concentrate or diluted with water prior to application.

Example 46

Permethrin Formula #3

Permethrin formula #3 is prepared by combining the ingredients of Table 26 in a 2-ounce stoppered bottle at ambient conditions.

This concentrate is diluted to 1/10, 1/100 and 1/1000, and all dilutions are clear upon preparation.

TABLE 26

Permethrin formula #3 of Example 46

| ingredient | mass (g) |
|---|---|
| matrix composition #1 | 80 |
| benzyl benzoate | 10 |
| permethrin[1] | 10 |
| total | 100 |

[1]FMC, Guarda (Google it)

Example 47

Permethrin Formula #4

Permethrin formula #4 is prepared by combining the ingredients of Table 27 in a 2-ounce stoppered bottle at ambient conditions.

This concentrate is diluted to 1/10, 1/100 and 1/1000, and all dilutions are clear upon preparation.

This composition can be used to control termite and other insects.

TABLE 27

| Permethrin formula #4 of Example 47 | |
|---|---|
| ingredient | mass (g) |
| matrix composition #1 | 70 |
| benzyl benzoate | 15 |
| permethrin | 15 |
| total | 100 |

Example 48

Permethrin Formula #5

Permethrin formula #5 is prepared by combining the ingredients of Table 28 in a 2-ounce stoppered bottle.

This concentrate is diluted to 1/10, 1/100 and 1/1000. All concentrates and clear dilutions remain clear for a period of 4 weeks. Results of Examples 47 and 48 illustrate that active ingredients soluble in benzyl benzoate along with matrix compositions can be formulated.

This composition can be used to control termite and other insects.

TABLE 28

| Permethrin formula #5 of Example 48 | |
|---|---|
| ingredient | mass (g) |
| matrix composition #1 | 60 |
| benzyl benzoate | 20 |
| permethrin | 20 |
| total | 100 |

Example 49

Uses of Permethrin Formulas #3-#5

Permethrin formulas #3-5 are used for termite control in construction sites and in consumer applications, as well as an additive in shampoo matrices to provide control of lice and other parasites.

Example 50

Microemulsions of Hydrophobic Materials

Matrix compositions #1-#8, and #10 are combined with various hydrophobic materials, such as bioactive organic compounds, natural and synthetic oils, waxes, monomers, perfumes, biocides, herbicides, insecticides, fungicides, plant growth regulators, preservatives, disinfectants, and other materials.

Microemulsions of the hydrophobic materials are formed.

Example 51

Microemulsions of Hydrophobic Materials

Matrices of Example 28 or Example 29 are modified to include additional solvent(s), such as polyalkylene polyols (e.g., polyethylene glycols, polypropylene glycols, or copolymers thereof). One such example is the matrix composition #11 (Table 29), which incorporates PEG 600 with matrix composition #1 and N-octyl pyrrolidone.

These matrices can be combined with various hydrophobic materials, such as bioactive organic compounds, natural and synthetic oils, waxes, monomers, perfumes, biocides, herbicides, insecticides, fungicides, plant growth regulators, preservatives, disinfectants, and other materials. Diluted solutions of 1/10, 1/100 and 1/1000 are clear upon preparation.

Microemulsions of the hydrophobic materials are formed.

TABLE 29

| Matrix composition #11 of Example 51 | |
|---|---|
| ingredient | mass (g) |
| matrix composition #1 | 44 |
| N-octyl pyrrolidone[1] | 6 |
| PEG 600 | 50 |
| total | 100 |

[1]International Specialty Products

Example 52

Microemulsions of Hydrophobic Materials

Example 51 is repeated except 10 g of citral are dissolved in 90 g of matrix composition #1, 2, 3, or 4 (Table 30). Optionally, N-octyl pyrrolidone can be replaced with Hallcomid® M-8-10. Diluted solutions of 1/10, 1/100 and 1/1000 are clear.

TABLE 30

| Matrix composition #12 of Example 52 | |
|---|---|
| ingredient | mass (g) |
| matrix composition #1 | 72 |
| N-octyl pyrrolidone[1] | 18 |
| citral | 10 |
| total | 100 |

[1]International Specialty Products

Example 53

Microemulsions of Hydrophobic Materials

Example 52 is repeated except mild orange oil replaces citral. Diluted solutions of 1/10, 1/100 and 1/1000 are clear.

Example 54

Microemulsions of Hydrophobic Materials

Example 53 is repeated except 10 g valencia orange oil replaces mild orange oil. Diluted solutions of 1/10, 1/100 and 1/1000 are clear.

Example 55

Slimacide Formula and Use Thereof

The reactive product of Example 15, methylene bisthiocyanate, first is filtered and then is diluted with bis-N-ethyl pyrrolidone ether to 40% solids.

This concentrate is effective to treat and/or prevent slime formation in paper mills when it is diluted with water to about 50 ppm active to 2000 ppm active.

Example 56

Strobilurin Fungicidal Formulas and Uses Thereof

A fungicide solution for the Strobilurin class of fungicides (e.g., azoxystrobin, trifloxystrobin, kresoxim methyl, and Strobilurin A-H), alone or in combination with other Strobilurin or other fungicides, is prepared at 10% active in bis-N-ethyl pyrrolidone ether. Then, this solution is mixed with a blend of mixed alkyl pyrrolidones, surfactants, and water-insoluble polymers (Agrimax® 3HH, International Specialty Products, Wayne, N.J.) at a 1:1 weight ratio. The 5% active concentrate is diluted with water to 100 ppm Strobilurin.

The diluted fungicide solution exhibit excellent fungicide activity and stability. The concentrate also is stable against phase separation and recrystallization.

Example 57

Use in Agricultural Granule Coating

A granular composition for pre-emergent crop protection is produced by dissolving highly water insoluble pre-emergent herbicides in bis-N-ethyl pyrrolidone ether.

In a suitable granular carrier like montmerolinite kaolin, attaclay, and fumed silica applied in the soil at the use concentration to provide pre-emergent herbicide activity.

Example 58

Zinc Pyrithione Formula and Use Thereof

A formula is made containing an effective amount of zinc pyrithione with matrix composition #3, such as indicated in Table 31. This formula is added to a preformed shampoo matrix to produce a clear composition containing 1% zinc pyrithione.

The shampoo protects against dandruff and other fungal infestation.

TABLE 31

| Zinc pyrithione formula of Example 58 | |
|---|---|
| ingredient | mass (g) |
| matrix composition #3 | 75-95 |
| zinc pyrithione | 5-25 |
| total | 100 |

Example 59

Miconazole Formula and Use Thereof

A matrix is prepared containing 80% maleated linseed oil and neutralized using aminomethyl propanol (Bomol® 4N) and 20% bis-N-ethyl pyrrolidone ether. To this matrix is dissolved 10 parts of miconazole. Water is added to make an optically clear, 200 ppm-400 ppm miconazole preparation. The final proportions are indicated in Table 32.

This clear solution is absorbed onto fumed silica and is effective in application on toe nails to clear fungal infection.

TABLE 32

| Miconazole formula of Example 59 | |
|---|---|
| ingredient | concentration |
| self-emulsifying oil | 0.144%-0.288% |
| bis-N-ethyl pyrrolidone ether | 0.036%-0.072% |
| miconazole | 0.020%-0.040% |
| water | 99.800%-99.600% |
| total | 100.00% |

Example 60

Tebuconazole Formula

A tebuconazole formula is prepared by combining the ingredients of Table 33. On dilution with water to 1/100 a stable emulsion is produced.

The tebuconazole formula is stable and useful for application on plants for fungicidal activities.

TABLE 33

| Tebuconazole formula of Example 60 | |
|---|---|
| ingredient | concentration |
| tebuonazole[1] | 15-25% |
| matrix composition #4 | 75-85% |
| total | 100% |

Example 61

2-(thiocyanatomethylthio)-1,3-benzothiazole (TCMTB) Formula and Use Thereof Example 60 is repeated replacing tebuconazole with TCMTB (Table 34). This formula finds utility for application on plants, or for application on leather substrates to prevent fungus infestation during storage.

TABLE 34

| TCMTB formula of Example 61 | |
|---|---|
| ingredient | concentration |
| TCMTB | 15-25% |
| matrix composition #4 | 75-85% |
| total | 100% |

Example 62

Penconazole Formula and Use Thereof

A penconazole formula is made containing the ingredients and concentrations indicated in Table 35. Stable emulsions are obtained upon diluting the penconazole preparation in ratios of 1/100, and 1/1000 with water.

The diluted samples are effective in protecting wood from fungal attack.

TABLE 35

Penconazole formula of Example 62

| ingredient | concentration |
|---|---|
| bis-N-ethyl pyrrolidone ether | 10% |
| N-octyl pyrrolidone (Surfadone ® LP-100) | 14% |
| ethoxylated castor oil (30 EO) | 14% |
| sodium lauryl sulfate | 14% |
| penconazole | 14% |
| water | 34% |
| total | 100% |

Example 63

Oxytetracycline Formula and Uses Thereof

An effective amount of one or more antibiotics, such as oxytetracycline dihydrate and/or doxycycline hyclate, is dissolved in bis-N-ethyl pyrrolidone ether, along with a pharmaceutical grade of polylactate, polyglycolate, and/or poly(lactate-co-glycolate) as depositing agent. Other suitable pharmaceutical excipients may be included, such as those disclosed in *Pharmaceutical Excipients*, R. C. Rowe, et al. (eds.), Pharmaceutical Press and American Pharmaceutical Association, 2003, which is incorporated herein its entirety by reference.

The composition may be useful in many varied applications, such as an oral care antibiotic during and after oral surgery, infections of the respiratory and urinary tracts, eyes, and skin of both humans and animals.

Example 64

Doxycycline Hyclate Formula and Uses Thereof

An effective amount of doxycycline hyclate is dissolved in bis-N-ethyl pyrrolidone ether, along with a pharmaceutical grade of aliphatic polyesters as depositing agent.

The composition may be used in treating chronic prostatitis, sinusitis, Syphilis, Chlamydia, pelvic inflammatory disease, acne, rosacea, and Rickettsial infections.

Example 65

Indomethacin Transdermal Patch and Uses Thereof

A microemulsion of about 10% indomethacin is prepared with bis-N-ethyl pyrrolidone ether along with about 50% octyl lactate and about 40% sorbitan fatty acid esters and food-grade emulsifiers (e.g., Span® 20 and Tween® 80). The composition is diluted with water at a ratio of 1/10. The aqueous microemulsion is absorbed onto fumed silica, then the composition is cast as a denial patch on a suitable substrate.

The patch is effective in reducing fever, pain, stiffness, and/or swelling.

Example 66

Felbinac, Ketoprofen, and/or Flurbiprofen Transdermal Patches and Uses Thereof

Example 65 is repeated, replacing indomethacin with an effective amount of felbinac, ketoprofen, and/or flurbiprofen.

The patches are effective in reducing fever, pain, stiffness, and/or swelling.

Example 67

Acne/Athletic Foot Ointment/Powder and Uses Thereof

Stable solutions of hydrogen peroxide in bis-N-ethyl pyrrolidone ether are prepared by removing water by distillation from a mixture of hydrogen peroxide and bis-N-ethyl pyrrolidone ether at a reduced pressure. Addition of poly(N-vinyl-2-pyrrolidone) further stabilizes the peroxide. The concentrated hydrogen peroxide is impregnated onto silica gel or a suitable carrier.

The formulation is effective as a disinfecting powder, to control skin infections, e.g., of the foot, face, or back.

Additional components like talc, fragrances and emollients can be introduced for treatment of acne.

Example 68

Avermectin Formulations and Uses Thereof

Avermectin formulations are created by dissolving an effective amount of it in bis-N-ethyl pyrrolidone ether, along with effective amounts of benzoic acid or citric acid as a buffering agent (e.g., 1%-5%), the ether solvent acting as a base for the buffering effect. Additional formulary ingredients can be used, such as buffering agents and rheology modifiers. The avermectin-stabilized compositions may be used as a shampoo additive or as an injectible.

The bis-N-ethyl pyrrolidone ether injectible formulation of avermectin is effective in providing broad range treatment against endoparasites and exoparasites, for example, head lice or veterinary injectibles for use on hoofed animals.

What is claimed is:

1. A compound represented by the structure:

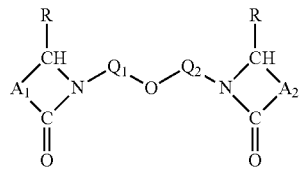

wherein:
one of $A_1$ and $A_2$ is —$CH_2CH_2$— and the other is —$CH_2CH_2CH_2$—;
said $Q_1$ and $Q_2$ are independently selected from a linear or branched $C_{1-6}$alkyl; and
each said R is independently selected from the group consisting of hydrogen, and $C_{1-4}$ alkyl.

2. The compound according to claim 1 selected from the group consisting of:

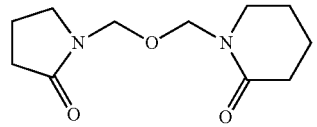

-continued

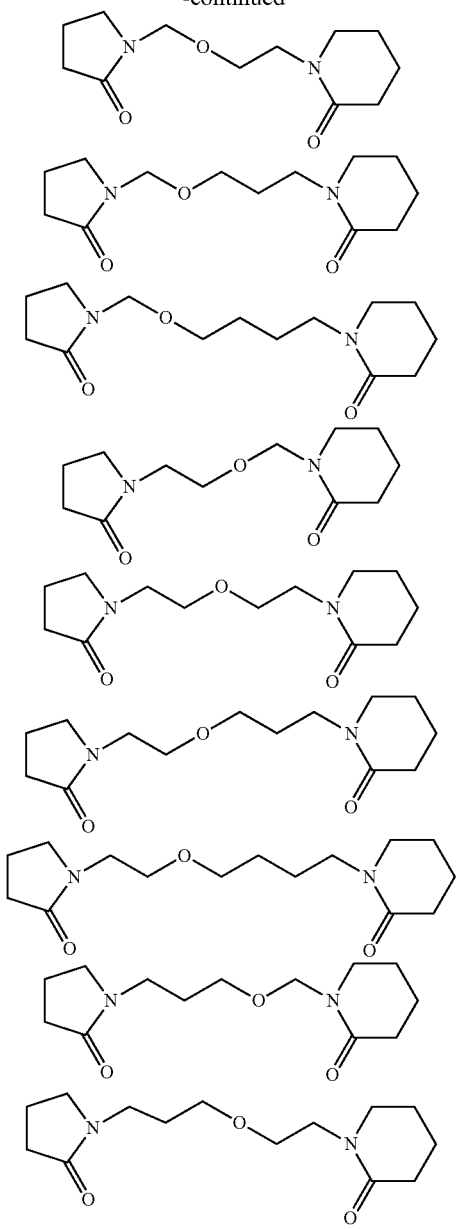

-continued

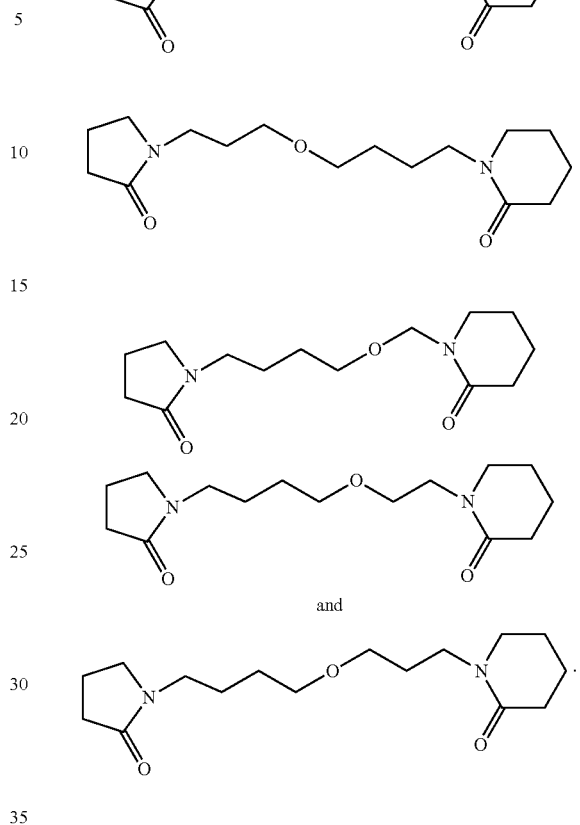

and

3. A sun care composition comprising the compound of claim 1 and one or more UV absorbers selected from the group consisting of: p-aminobenzoic acid (PABA), Padimate O, ensulizole, cinoxate, benzophenone-3, enzophenone-8, homosalate, meradimate, octocrylene, 2-ethylhexyl-p-methoxycinnamate, octyl salicylate, sulisobenzone, trolamine salicylate, avobenzone, ecamsule, titanium dioxide, zinc oxide, 4-methylbenzylidene, Tinosorb M, neo heliopan AP, mexoryl XL, benzophenone-9, Uvinul T150, Uvinul A Plus, Uvasorb HEB, Parsol SLX, isopentenyl-4-methoxycinnamate, and combinations thereof.

\* \* \* \* \*